(12) United States Patent
Shima et al.

(10) Patent No.: US 6,825,200 B1
(45) Date of Patent: Nov. 30, 2004

(54) SUBSTITUTED DIPEPTIDES HAVING NOS INHIBITING ACTIVITY

(75) Inventors: Ichiro Shima, Osaka (JP); Takehiko Ohkawa, Osaka (JP); Kazuhiko Ohne, Osaka (JP); Kentaro Sato, Osaka (JP); Naoki Ishibashi, Osaka (JP); Kenichiro Imamura, Osaka (JP)

(73) Assignee: Fujisawa Pharmaceutical Co., Ltd., Osaka-shi (JP)

( * ) Notice: Subject to any disclaimer, the term of this patent is extended or adjusted under 35 U.S.C. 154(b) by 0 days.

(21) Appl. No.: 10/111,412

(22) PCT Filed: Oct. 27, 2000

(86) PCT No.: PCT/JP00/07579
§ 371 (c)(1),
(2), (4) Date: May 6, 2002

(87) PCT Pub. No.: WO01/32690
PCT Pub. Date: May 10, 2001

(30) Foreign Application Priority Data

Nov. 4, 1999  (AU) .............................................. PQ 3868

(51) Int. Cl.⁷ .................... A61K 31/496; C07D 401/12; C07D 405/14; C07D 417/14
(52) U.S. Cl. .............................. 514/253.01; 514/253.1; 514/253.11; 644/360; 644/364
(58) Field of Search ................................ 544/360, 364; 514/253.01, 253.1, 253.11

(56) References Cited

U.S. PATENT DOCUMENTS 6,069,162 A    5/2000  Itoh et al.

FOREIGN PATENT DOCUMENTS

WO    96 16981    6/1996

OTHER PUBLICATIONS

Fretland et al. Current Pharmaceutical Design vol. 3,pp.447–462 (1997).*

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention a compound represented by the formula (I):

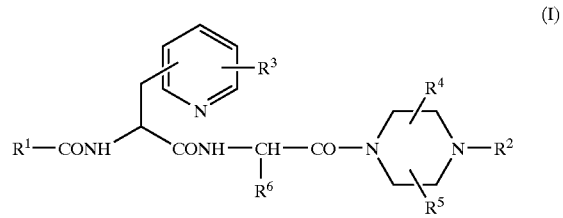

where the structural variables $R^1$–$R^6$ are defined herein.

19 Claims, No Drawings

SUBSTITUTED DIPEPTIDES HAVING NOS INHIBITING ACTIVITY

TECHNICAL FIELD

This invention relates to new peptide compounds and pharmaceutically acceptable salts thereof which are useful as medicament.

BACKGROUND ART

Some peptide compounds have been known as described in, for example, EP 0 394 989 A2, WO96/16981 and JP-A-10-81671.

DISCLOSURE OF INVENTION

This invention relates to new peptide compounds.

One object of this invention is to provide the new and useful peptide compounds and pharmaceutically acceptable salts thereof that possess a strong inhibitory activity on the production of nitric oxide (NO).

Another object of this invention is to provide a process for the preparation of the peptide compounds and salts thereof.

A further object of this invention is to provide a pharmaceutical composition comprising said peptide compound or a pharmaceutically acceptable salt thereof.

Still further object of this invention is to provide a use of said peptide compounds or pharmaceutically acceptable salts thereof as a medicament for prophylactic and therapeutic treatment of NO-mediated diseases including respiratory diseases such as adult respiratory distress syndrome (ARDS) and asthma; cardiovascular diseases such as cardiovascular ischemia, myocarditis, heart failure, hypotension and atherosclerosis; endocrine diseases such as diabetes (e.g., insulin-dependent diabetes mellitus, etc.), complications of diabetes mellitus (e.g., diabetic nephropathy, diabetic retinopathy, diabetic neuropathy, etc.) and gout; renal diseases such as glomerulonephritis and renal failure; gastrointestinal diseases such as peptic ulcer and inflammatory bowel disease (e.g., ulcerative colitis, chronic colitis, etc.); pancreatic diseases such as pancreatitis; hepatic diseases such as hepatitis and liver cirrhosis; diseases of bone or joint such as synovitis, arthritis, osteoarthritis, osteoporosis; autoimmune diseases such as rheumatoid arthritis, systemic lupus erythematosus and multiple sclerosis; dermal diseases such as dermatitis and eczema; cancer such as solid tumors and metastasis; rejection by organ transplantation; shock (e.g., septic shock, etc.); sepsis-induced systemic inflammatory response syndrome; and sexual dysfunction such as male sexual dysfunction (e.g., erectile dysfunction) and female sexual dysfunction (e.g., orgasmic dysfunction related to clitoral disturbances) in human being and animals.

The object peptide compounds of the present invention are novel and can be represented by the following general formula (I):

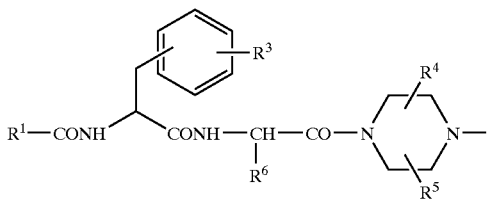

wherein
$R^1$ is benzofuranyl substituted by halogen, or styryl substituted by halogen,
$R^2$ is phenyl, pyridyl, thienyl or thiazolyl, each of which is optionally substituted by one or more substituents selected from the group consisting of lower alkyl, lower alkoxy, halogen and trihalo(lower)alkyl, or lower alkyl optionally substituted by one or more halogen atoms,
$R^3$ is hydrogen or lower alkoxy,
$R^4$ and $R^5$ are the same or different and each is hydrogen, lower alkyl or optionally protected hydroxy(lower)alkyl, and
$R^6$ is hydrogen or lower alkyl.

Suitable pharmaceutically acceptable salts of the object compound (I) are conventional non-toxic salts and include, for example, a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); and a salt with a basic or acidic amino acid (e.g., arginine, aspartic acid, gultamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "halogen" includes, for example, fluorine, bromine, chlorine and iodine.

"Styryl substituted by halogen" means styryl which has halogen atom as a substituent on the benzene ring. Suitable examples of "styryl substituted by halogen" include 2-(2-chlorophenyl)ethenyl, 2-(3-chlorophenyl)ethenyl, 2-(4-chlorophenyl)ethenyl, 2-(2-bromophenyl)ethenyl, 2-(3-bromophenyl)ethenyl, 2-(4-bromophenyl)ethenyl, 2-(2-fluorophenyl)ethenyl, 2-(3-fluorophenyl)ethenyl, 2-(4-fluorophenyl)ethenyl, and the like.

Suitable "lower alkyl" and "lower alkyl" moiety in the terms "trihalo(lower)alkyl" and "hydroxy(lower)alkyl" include straight or branched alkyl having 1 to 6 carbon atom(s), such as methyl, ethyl, propyl, isopropyl, butyl, isobutyl, sec-butyl, tert-butyl, pentyl, tert-pentyl and hexyl, in which more preferred one is $C_1$–$C_4$ alkyl.

Suitable "lower alkoxy" includes straight or branched alkoxy having 1 to 6 carbon atom(s), such as methoxy, ethoxy, propoxy, isopropoxy, butoxy, isobutoxy, sec-butoxy, tert-butoxy, pentyloxy, tert-pentyloxy and hexyloxy, in which more preferred one is $C_1$–$C_4$ alkoxy.

Suitable examples of "trihalo(lower)alkyl" include trifluoromethyl, trichloromethyl, tribromomethyl, 2,2,2-trifluoroethyl and 3,3,3-trifluoropropyl, in which more preferred one is trifluoromethyl.

"Lower alkyl optionally substituted by one or more halogen atoms" includes lower alkyl and halo(lower)alkyl. Suitable "halo(lower)alkyl" includes lower alkyl substituted by 1 to 3 halogen atoms such as trifluoromethyl, trichloromethyl, tribromomethyl, 2,2,2-trifluoroethyl and 3,3,3-trifluoropropyl, in which more preferred one is trihalo (lower)alkyl.

"Optionally protected hydroxy(lower)alkyl" includes hydroxy(lower)alkyl and protected hydroxy(lower)alkyl. Suitable examples of hydroxy-protecting group include lower alkyl (e.g., methyl, ethyl, propyl, isopropyl, butyl, sec-butyl, isobutyl, tert-butyl, pentyl, neopentyl, hexyl, etc.), acyl such as lower alkanoyl optionally substituted by one to three halogen atoms (e.g., formyl, acetyl, propanoyl, butanoyl, 2-methylpropanoyl, pentanoyl, 2,2-dimethylpropanoyl, hexanoyl, trichloroacetyl, trifluoroacetyl, etc.), optionally substituted phenyl(lower)alkyl, for example, mono(or di or tri)phenyl(lower)alkyl optionally substituted by nitro or lower alkoxy (e.g., benzyl, 4-nitrobenzyl, 4-methoxybenzyl, benzhydryl, trityl, etc.), trisubstituted silyl [e.g., tri(lower)alkylsilyl (e.g., trimethylsilyl, tert-butyldimethylsilyl, etc.), etc.], tetrahydropyranyl and the like.

Suitable "hydroxy(lower)alkyl" includes hydroxy($C_1$–$C_6$)alkyl such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and 6-hydroxyhexyl.

Suitable "protected hydroxy(lower)alkyl" includes lower alkoxy(lower)alkyl such as ($C_1$–$C_6$)alkoxy($C_1$–$C_6$)alkyl, for example, methoxymethyl, 1-methoxyethyl, 2-methoxyethyl, 1-methoxypropyl, 2-methoxypropyl, 3-methoxypropyl, ethoxymethyl, 2-ethoxyethyl, 3-ethoxypropyl and propoxymethyl.

Phenyl, pyridyl, thienyl or thiazolyl at $R^2$ is optionally substituted by one or more, preferably one to three, substituents selected from the group consisting of lower alkyl, lower alkoxy, halogen and trihalo(lower)alkyl.

Suitable "amino-protecting group" includes, for example, acyl and conventional protecting group such as mono(or di or tri)aryl(lower)alkyl, for example, mono(or di or tri)phenyl (lower)alkyl (e.g., benzyl, trityl, etc.). Suitable examples of said acyl include aliphatic acyl such as lower alkanoyl which may be substituted by one to three halogen atoms (e.g., formyl, acetyl, propanoyl, butanoyl, 2-methylpropanoyl, pentanoyl, 2,2-dimethylpropanoyl, hexanoyl, trichloroacetyl, trifluoroacetyl, etc.), lower alkoxycarbonyl (e.g., methoxycarbonyl, ethoxycarbonyl, tert-butoxycarbonyl, tert-pentyloxycarbonyl, etc.), aryl(lower)alkoxycarbonyl [e.g., phenyl(lower)-alkoxycarbonyl (e.g., benzyloxycarbonyl, etc.), etc.] and the like.

Suitable "carboxy-protecting group" includes, for example, lower alkyl (e.g., methyl, ethyl, propyl, isopropyl, butyl, sec-butyl, isobutyl, tert-butyl, pentyl, neopentyl, hexyl, etc.), optionally substituted phenyl(lower)alkyl, for example, mono(or di or tri)phenyl(lower)alkyl which may be substituted by nitro (e.g., benzyl, 4-nitrobenzyl, benzhydryl, trityl, etc.) and the like.

The object compound (I) of the present invention can be prepared by the following processes.

Process (1)

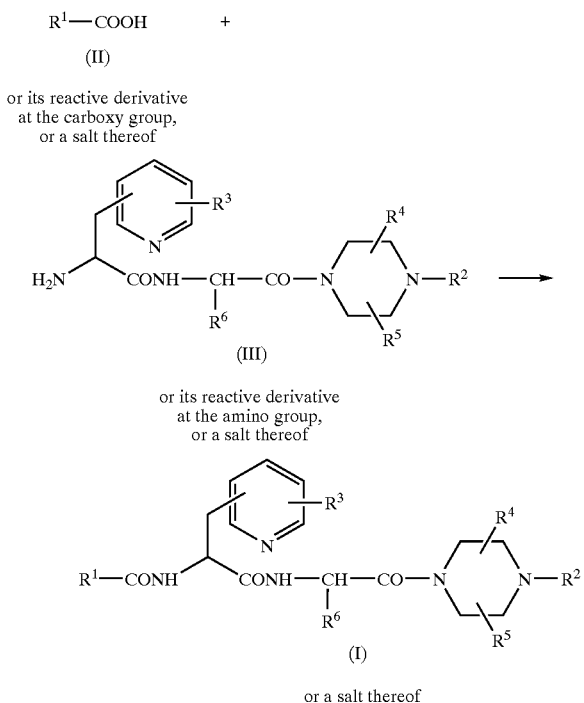

Process (2)

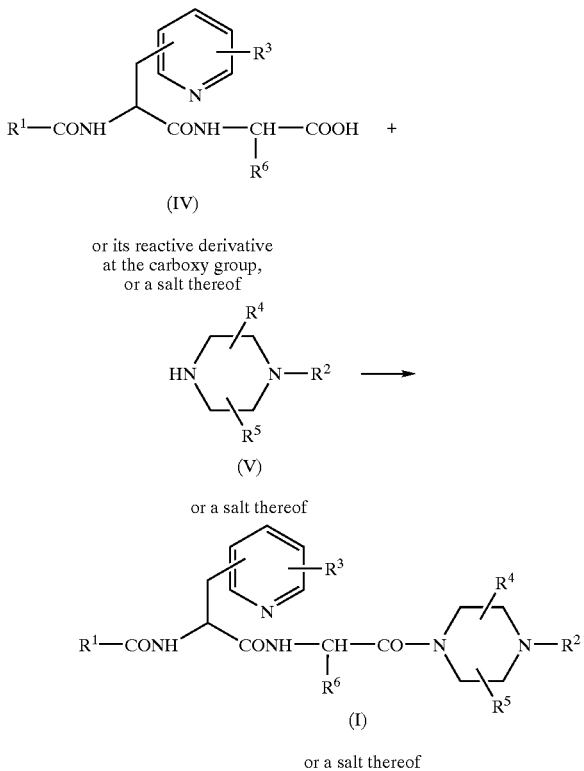

wherein $R^1$, $R^2$, $R^3$, $R^4$, $R^5$ and $R^6$ are each as defined above.

The starting compounds can be prepared by the following processes.
Process (A)
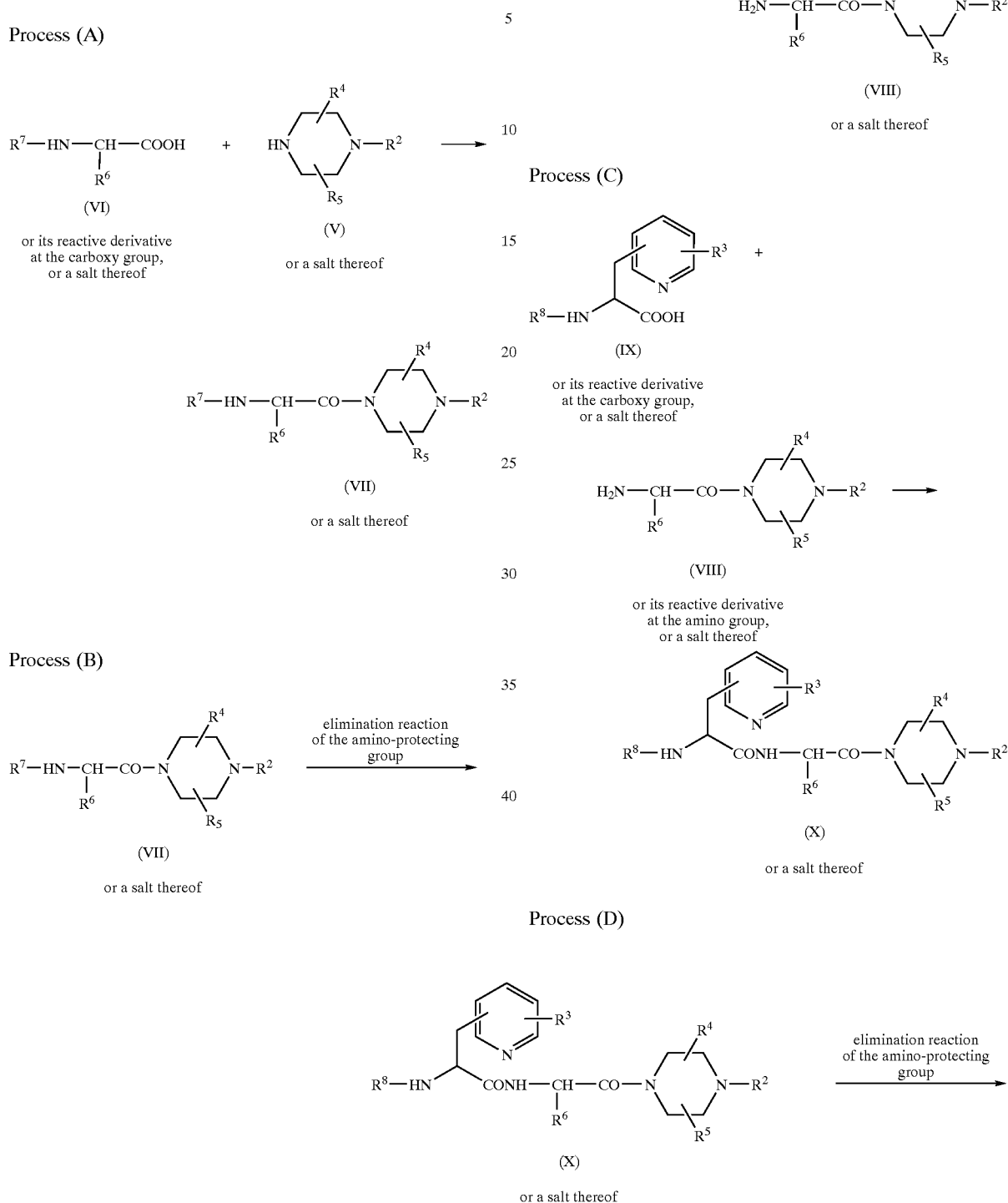
Process (B)
Process (C)
Process (D)

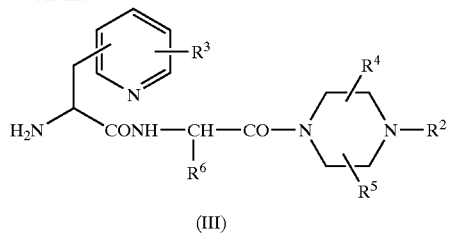
(III)
or a salt thereof
Process (E)
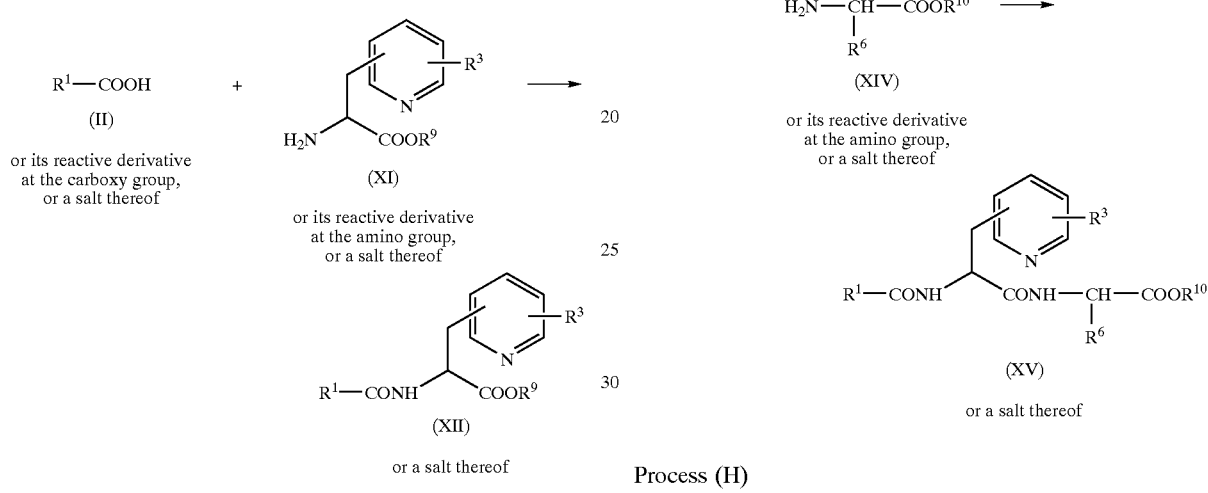
Process (F)
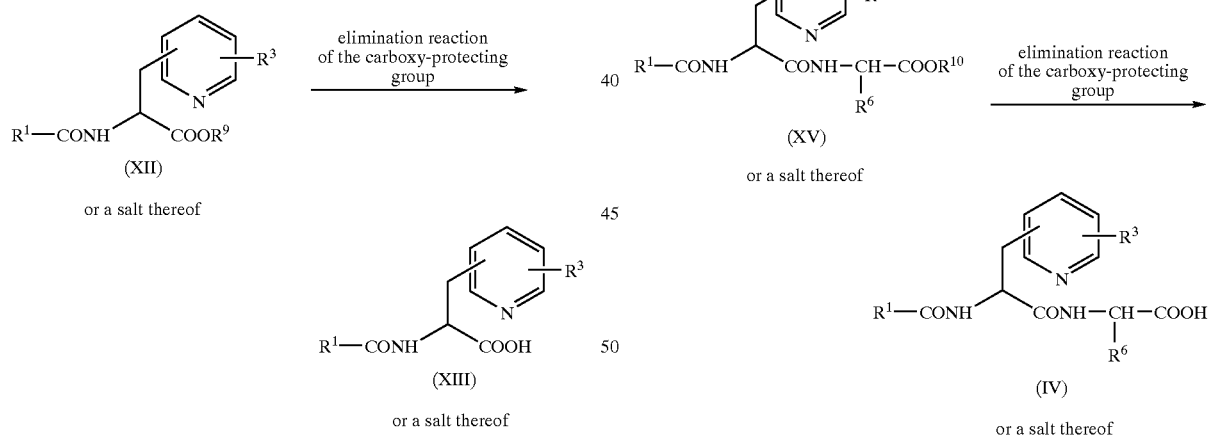
Process (G)
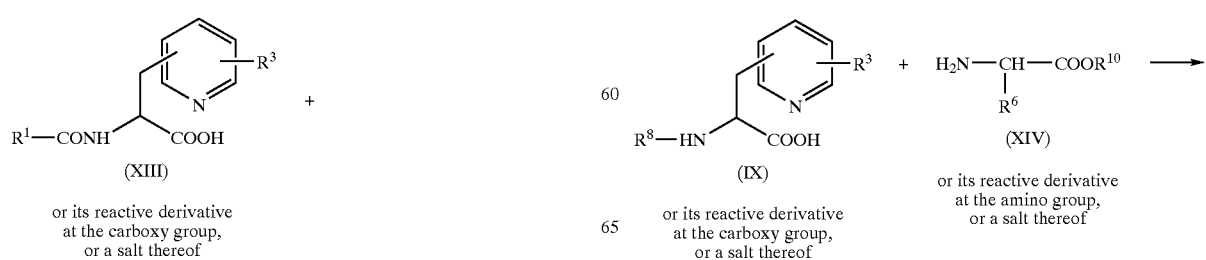

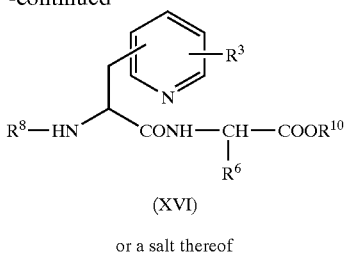

(XVI)

or a salt thereof

Process (J)

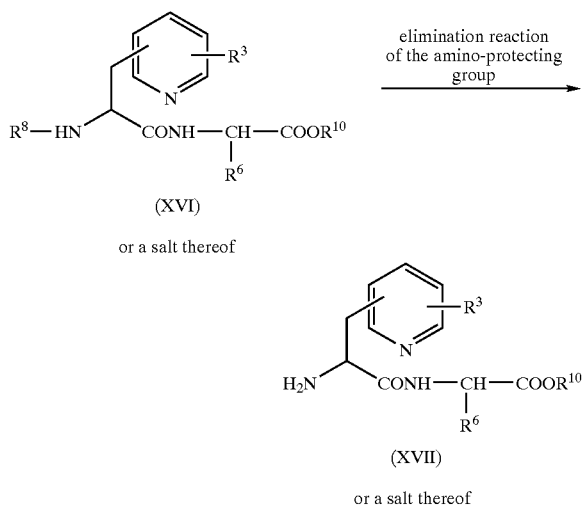

Process (K)

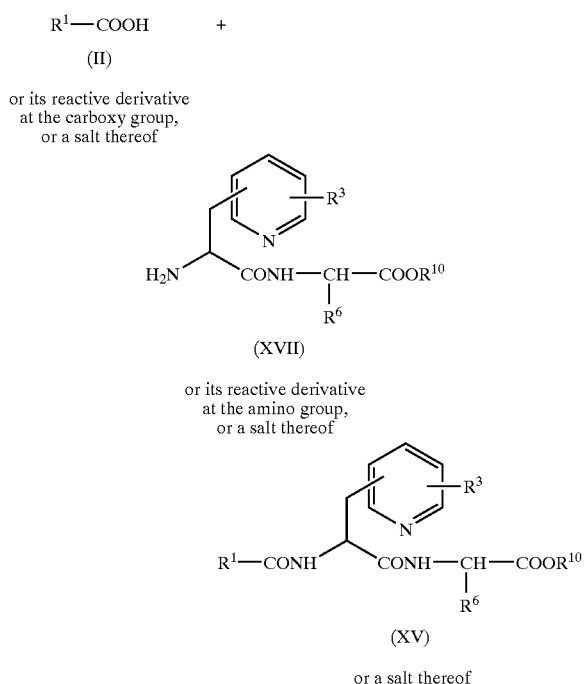

wherein $R^1$, $R^2$, $R^3$, $R^4$, $R^5$ and $R^6$ are each as defined above, $R^7$ and $R^8$ are each amino-protecting group, and $R^9$ and $R^{10}$ are each carboxy-protecting group.

The processes for preparing the object compound are explained in detail in the following.

Process (1)

The compound (I) or a salt thereof can be prepared by reacting the compound (II) or its reactive derivative at the carboxy group, or a salt thereof with the compound (III) or its reactive derivative at the amino group, or a salt thereof.

Suitable reactive derivative of the compound (III) includes Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as N,O-bis(trimethylsilyl)acetamide, N-trimethylsilylacetamide or the like; a derivative formed by the reaction of the compound (III) with phosphorus trichloride or phosgene.

Suitable reactive derivative of the compound (II) includes an acid halide, an acid anhydride and an activated ester. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.), and aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl $[(CH_3)_2N^+=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.); or an ester with an N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.). These reactive derivatives can optionally be selected from them according to the kind of the compound (II) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (II) is used in free acid form or its salt form in the reaction, the reaction is preferably carried out in the presence of a conventional condensing agent such as N,N'-dicyclohexylcarbodiimide; N-cyclohexyl-N'-morpholinoethyl-carbodiimide; N-cyclohexyl-N'-(4-diethylaminocyclohexyl)-carbodiimide; N,N'-diisopropylcarbodiimide; N-ethyl-N'-(3-dimethylaminopropyl)carbodiimide; N,N-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl) isoxazolium hydroxide intramolecular salt; 1-(p- chlorobenzenesulfonyloxy)-6-chloro-1H-benzotriazole; so-called Vilsmeier reagent prepared by the reaction of N,N-dimethylformamride with thionyl chloride, phosgene, phosphorus oxychloride, etc.; or the like.

The reaction may also be carried out in the presence of an organic or inorganic base such as an alkali metal bicarbonate, tri(lower)alkylamine, pyridine, N-(lower) alkylmorpholine, N,N-di(lower)alkylbenzylamine, or the like.

The reaction temperature is not critical, and the reaction is usually carried out under cooling to heating.

Process (2)

The compound (I) or a salt thereof can be prepared by reacting the compound (IV) or its reactive derivative at the carboxy group, or a salt thereof with the compound (V) or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (A)

The compound (VII) or a salt thereof can be prepared by reacting the compound (VI) or its reactive derivative at the carboxy group, or a salt thereof with the compound (V) or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (B)

The compound (VIII) or a salt thereof can be prepared by subjecting the compound (VII) or a salt thereof to elimination reaction of the amino-protecting group.

Suitable method of this elimination reaction includes conventional one such as hydrolysis, reduction and the like.

(i) For Hydrolysis:

The hydrolysis is preferably carried out in the presence of a base or an acid including Lewis acid.

Suitable base includes an inorganic base and an organic base such as an alkali metal (e.g., sodium, potassium, etc.), an alkaline earth metal (e.g., magnesium, calcium, etc.), the hydroxide or carbonate or hydrogencarbonate thereof, trialkylamine (e.g., trimethylamine, triethylamine, etc.), picoline, 1,5-diazabicyclo[4.3.0]non-5-one, or the like.

Suitable acid includes an organic acid (e.g., formic acid, acetic acid, propionic acid, trichloroacetic acid, trifluoroacetic acid, etc.), and an inorganic acid (e.g., hydrochloric acid, hydrobromic acid, sulfuric acid, hydrogen chloride, hydrogen bromide, etc.).

The elimination using. Lewis acid such as trihaloacetic acid (e.g., trichloroacetic acid, trifluoroacetic acid, etc.), or the like is preferably carried out in the presence of cation trapping agents (e.g., anisole, phenol, etc.). This reaction is usually carried out without solvent.

The reaction may be carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or a mixture thereof.

The reaction temperature is not critical and the reaction is usually carried out under cooling to warming.

(ii) For Reduction:

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, palladium hydroxide on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or a mixture thereof.

Additionally, in case that the above-mentioned acids to be used in chemical reduction are in a liquid state, they can also be used as a solvent.

The reaction temperature of this reduction is not critical and the reaction is usually carried out under cooling to warming.

Process (C)

The compound (X) or a salt thereof can be prepared by reacting the compound (IX) or its reactive derivative at the carboxy group, or a salt thereof with the compound (VIII) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (D)

The compound (III) or a salt thereof can be prepared by subjecting the compound (X) or a salt thereof to elimination reaction of the amino-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (E)

The compound (XII) or a salt thereof can be prepared by reacting the compound (II) or its reactive derivative at the carboxy group, or a salt thereof with the compound (XI) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of process (1).

Process (F)

The compound (XIII) or a salt thereof can be prepared by subjecting the compound (XII) or a salt thereof to elimination reaction of the carboxy-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (G)

The compound (XV) or a salt thereof can be prepared by reacting the compound (XIII) or its reactive derivative at the carboxy group, or a salt thereof with the compound (XIV) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (H)

The compound (IV) or a salt thereof can be prepared by subjecting the compound (XV) or a salt thereof to elimination reaction of the carboxy-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (I)

The compound (XVI) or a salt thereof can be prepared by reacting the compound (IX) or its reactive derivative at the carboxy group, or a salt thereof with the compound (XIV) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Process (J)

The compound (XVII) or a salt thereof can be prepared by subjecting the compound (XVI) or a salt thereof to elimination reaction of the amino-protecting group.

This reaction can be carried out in a similar manner to the reaction in the aforementioned Process (B), and therefore the reagents to be used and reaction conditions (e.g., solvent, reaction temperature, etc.) can be referred to those of Process (B).

Process (K)

The compound (XV) or a salt thereof can be prepared by reacting the compound (II) or its reactive derivative at the carboxy group, or a salt thereof with the compound (XVII) or its reactive derivative at the amino group, or a salt thereof.

This reaction can be carried out in a similar manner to the reaction in the aforementioned Process (1), and therefore the reagents to be used and reaction conditions (e.g., solvent, reaction temperature, etc.) can be referred to those of Process (1).

Suitable salts of the starting compounds and their reactive derivatives in Processes (1) and (2) and Processes (A) to (K) can be referred to the ones as exemplified for the compound (I).

The compounds obtained by the above process can be isolated and purified by a conventional method such as pulverization, recrystallization, column chromatography, reprecipitation, or the like.

It is to be noted that the compound (I) and the other compounds may include one or more stereoisomer(s) such as optical isomer(s) and geometrical isomer(s) due to asymmetric carbon atom(s) and double bond(s), and all of such isomers and mixtures thereof are included within the scope of this invention.

The object compounds (I) and pharmaceutically acceptable salts thereof include solvates [e.g., enclosure compounds (e.g., hydrate, etc.)].

The object compounds (I) and pharmaceutically acceptable salts thereof possess a strong inhibitory activity on the production of nitric oxide (NO).

Accordingly, the object compounds (I) and pharmaceutically acceptable salts thereof are expected to possess a nitric oxide synthase (NOS)-inhibitory activity or a NOS-production inhibitory activity.

Accordingly, the object compounds (I) and pharmaceutically acceptable salts thereof are useful for prevention and/or treatment of NO-mediated diseases in human being and animals, including respiratory diseases such as adult respiratory distress syndrome (ARDS) and asthma; cardiovascular diseases such as cardiovascular ischemia, myocarditis, heart failure, hypotension and atherosclerosis; endocrine diseases such as diabetes (e.g., insulin-dependent diabetes mellitus, etc.), complications of diabetes mellitus (e.g., diabetic nephropathy, diabetic retinopathy, diabetic neuropathy, etc.) and gout; renal diseases such as glomerulonephritis and renal failure; gastrointestinal diseases such as peptic ulcer and inflammatory bowel disease (e.g., ulcerative colitis, chronic colitis, etc.); pancreatic diseases such as pancreatitis; hepatic diseases such as hepatitis and liver cirrhosis; diseases of bone or joint such as synovitis, arthritis, osteoarthritis, osteoporosis; autoimmune diseases such as rheumatoid arthritis, systemic lupus erythematosus and multiple sclerosis; dermal diseases such as dermatitis and eczema; cancer such as solid tumors and metastasis; rejection by organ transplantation; shock (e.g., septic shock, etc.); and sepsis-induced systemic inflammatory response syndrome.

The object compounds (I) and pharmaceutically acceptable salts thereof are also useful for prevention and/or treatment of No-mediated nervous diseases including central nervous system diseases such as CNS disorders, cerebrovascular diseases (e.g., cerebral infarction, cerebral ischemia, cerebral hemorrhage, etc.), migraine, Alzheimer's disease; peripheral nervous system diseases such as neuritis, pain (e.g., postherpetic neuralgia, reflex sympathetic dystrophy (RSD), causalgia, deafferentation pain syndrome, neuropathic pain, etc.), allodynia, hyperalgesia, neurological disorders and neuroprotection; Parkinson's disease; and amyotrophic lateral sclerosis.

Additionally, the object compounds (I) and pharmaceutically acceptable salts thereof are useful for treatment of sexual dysfunction such as male sexual dysfunction including erectile dysfunction, and female sexual dysfunction including orgasmic dysfunction related to clitoral disturbances.

Further, the object compounds (I) and pharmaceutically acceptable salts thereof are useful for prevention and/or treatment of NO-mediated ophthalmic diseases, including conjunctive diseases such as conjunctivitis (e.g., allergic conjunctivitis, vernal conjunctivitis, keratoconjunctivitis sicca, viral conjunctivitis, bacterial conjunctivitis, etc.); uveal diseases such as uveitis (e.g., Behcet disease, Harada disease, sympathetic ophthalmia, sarcoidosis, diabetic iritis, etc.); scleral diseases such as scleritis; corneal diseases such as corneal neovascularization, keratitis, corneal edema, corneal opacity, corneal dystrophy, keratoconus and neuroparalytic keratitis; retinal, vitreous diseases such as diabetic retinopathy, retinal artery occlusion, retinal vein occlusion, central serous chorioretinopathy, central hemorrhagic chorioretinitis, macular degeneration (e.g., age-related macular degeneration, etc.), retinal detachment, retinal pigmentary degeneration, macular neovascularization, macular hole, proliferative vitreoretinopathy, vitreous hemorrhage and vitreous opacity; lens diseases such as cataract (e.g., senile cataract, traumatic cataract, diabetic cataract, atopic cataract, etc.); glaucoma such as primary open-angle glaucoma, primary angle-closure glaucoma, normal tension glaucoma and neovascular glaucoma; ocular hypertension; vision disorders such as amblyopia, color vision defect and night blindness; refractive errors such as astigmatism, hyperopia, myopia and presbyopia; and lacrimal apparatus diseases such as dry eye syndromes, lacrimal duct obstruction and dacryocystitis.

In order to illustrate the usefulness of the object compound (I), the pharmacological test result of the compound (I) is shown in the following.

Test Compound:

Compound (a): 5-Chloro-N-[(1S)-2-[[2-[4-(4-chlorophenyl)-1-piperazinyl]-2-oxoethyl]amino]-2-oxo-1-(2-pyridylmethyl)ethyl]-1-benzofuran-2-carboxamide Compound (b): (2E)-3-(4-Chlorophenyl)-N-[(1S)-2-[[2-((2S)-2-methyl-4-phenyl-1-piperazinyl)-2-oxoethyl]amino]-2-oxo-1-(2-pyridylmethyl)ethyl]-2-propenamide Compound (c): (2E)-3-(4-Chlorophenyl)-N-[(1S)-2-[[2-[(2R,6S)-2,6-dimethyl-4-(4-methylphenyl)-1-piperazinyl]-2-oxoethyl]amino]-2-oxo-1-(2-pyridylmethyl)ethyl]-2-propenamide Compound (d): (2E)-3-(4-Chlorophenyl)-N-[(1S)-2-oxo-2-[[2-oxo-2-[4-(3,3,3-trifluoropropyl)-1-piperazinyl]ethyl]amino]-1-(2-pyridylmethyl) ethyl]-2-propenamide Compound (e): (2E)-3-(4-Chlorophenyl)-N-[(1S)-2-oxo-2-[[2-oxo-2-[4-(4-trifluoromethylphenyl)-1-piperazinyl]ethyl]amino]-1-(2-pyridylmethyl)ethyl]-2-propenamide Compound (f): 5-Chloro-N-[(1S)-2-[[2-[4-(4-methoxyphenyl)-1-piperazinyl]-2-oxoethyl]amino]-2-oxo-1-(2-pyridylmethyl) ethyl]-1-benzofuran-2-carboxamide Test 1: Assay for Inhibitory Activity on the Production of Nitric Oxide The murine macrophage cell line RAW264.7 (American Type Culture Collection, No. TIB71) was used in this study. RAW264.7 cells were grown on F75 plastic culture flasks at 37° C., 5% in Dulbecco's modified Eagle's medium (DMEM) supplemented with L-glutamine, penicillin, streptomycin and 10% heat-inactivated fetal bovine serum. They were removed from culture flasks by rubber cell scraper and were centrifuged and resuspended in DMEM without phenol red. They were plated in 96-well microtiter plates ($10^5$ cells per well) and allowed to adhere over 2 hours. The test samples were added and the cells were preincubated for 1 hour. Thereafter the cells were activated with both of lipopolysaccharide (LPS) (1 µg/ml) and interferon γ (INF γ) (3 u/ml) for 18–24 hours. An equal volume of Griess reagent (1% sulfanilamide/0.1% N-naphthylethylenediamine dihydrochloride/2.5% $H_3PO_4$) was added and the cells were incubated at room temperature for 10 minutes. The absorbance was read at 570 nm using microplate reader and $NO_2^-$ was measured using $NaNO_2$ as a standard.

Test Result:

TABLE 1

| Test compound ($10^{-6}$ M) | Inhibition (%) |
|---|---|
| (a) | 100 |
| (b) | 100 |
| (c) | 100 |
| (d) | 100 |
| (e) | 99 |
| (f) | 100 |

Test 2: Protective Effect of the Compound (I) Combined with FK506 on Rat Cardiac Allograft Method:

Experiments were performed on male Lewis and ACI rats weighing 175–200 g. Rats were anesthetized with sodium pentobarbital (50 mg/kg, i.p.), and underwent allogeneic (Lewis donor to ACI recipient) heterotopic cardiac transplantation. Experimental groups were divided into single-drug group and combined-drug group. Single-drug dose of FK506, which was prepared in a manner similar to that disclosed in EP-0184162, was 0.32 mg/kg. Combined-drug dose was FK506 (0.32 mg/kg)+the compound (I) (10 mg/kg). The grafted hearts were monitored by daily palpation where complete rejection was defined as the cessation of palpable contractile activity. Each drug was suspended in a solution of 0.5% methylcellulose, and administered by daily gastric intubation in a volume of 5 ml/kg of body weight for 14 days.

The combination of the compound (I) and FK506 dramatically prolonged the graft survival.

The above experimental results indicate that the activity and/or efficacy of an immunosuppressant in rejection of transplantation can be remarkably and synergistically increased by administering compound (I) in combination, which has a strong inhibitory activity on the production of nitric oxide.

For therapeutic administration, the object compound (I) of the present invention and pharmaceutically acceptable salts thereof are used in the form of a conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee, suppository or ointment, or in a liquid form such as solution, suspension or emulsion for injection, intravenous drip, ingestion, eye drop, etc. If needed, there may be included in the above preparation auxiliary substance such as stabilizing agent, wetting or emulsifying agent, buffer or any other commonly used additives.

The effective ingredient may usually be administered in a unit dose of 0.001 mg/kg to 500 mg/kg, preferably 0.01 mg/kg to 10 mg/kg, 1 to 4 times a day. However, the above dosage may be increased or decreased according to age, body weight and conditions of the patient or administering method.

According to the present invention, a pharmaceutical composition comprising FK506 and the compound (I) or a pharmaceutically acceptable salt thereof is provided. A pharmaceutical composition comprising FK506 and the compound (I) or a pharmaceutically acceptable salt thereof is useful as an immunosuppressant. For example, the pharmaceutical composition of the present invention is useful for the prevention or treatment of rejection by organ transplantation.

When the compound (I) is used in combination with FK506, a ratio by weight of the compound (I) or a pharmaceutically acceptable salt thereof to FK506 is in the range of 0.1/1–1000/1, preferably in the range of 1/1–100/1.

The preferred embodiments of the peptide compound of the present invention represented by the general formula (I) are as follows.

1) The compound of the formula (I) wherein $R^1$ is benzofuranyl substituted by halogen.
2) The compound of the formula (I) wherein $R^1$ is styryl substituted by halogen.

3) The compound of the formula (I) wherein $R^2$ is phenyl, pyridyl, thienyl or thiazolyl, each of which is optionally substituted by one or more substituents selected from the group consisting of lower alkyl, lower alkoxy, halogen and trihalo(lower)alkyl, or trihalo(lower)alkyl.
4) The compound of the formula (I) wherein $R^2$ is phenyl optionally substituted by one or more substituents selected from the group consisting of lower alkyl, lower alkoxy, halogen and trihalo(lower)alkyl, or trihalo(lower)alkyl.
5) The compound of the formula (I) wherein $R^2$ is pyridyl, thienyl or thiazolyl, each of which is optionally substituted by one or more substituents selected from the group consisting of halogen and trihalo(lower)alkyl.
6) The compound of the formula (I) wherein $R^4$ and $R^5$ are the same or different and each is hydrogen, lower alkyl, hydroxy(lower)-alkyl or lower alkoxy(lower)alkyl.

The following Preparations and Examples are given for the purpose of illustrating the present invention in detail.

Preparation 1 tert-Butoxy-N-[2-[4-(4-chlorophenyl)-1-piperazinyl]-2-oxoethyl]formamide

To a suspension of 2-(tert-butoxycarbonylamino)acetic acid (16.3 g) and 1-(4-chlorophenyl)piperazine hydrochloride (21.7 g) in N,N-dimethylformamide (200 ml) were added 1-ethyl-3-(3-dimethylaminopropyl)carbodiimide hydrochloride (19.6 g) and N-hydroxybenzotriazole (13.8 g) at 0° C. To this suspension was added dropwise triethylamine (10.4 g). The mixture was stirred at room temperature for 20 hours. The reaction mixture was poured into ice-cold water and the resulting solid was collected by filtration. The solid was washed successively with saturated aqueous sodium hydrogencarbonate solution and water. The solid was dried to give the title compound (29 g).

$^1$H-NMR (300 MHz, CDCl$_3$) δ 3.09–3.18 (m, 4H), 3.51–3.59 (m, 2H), 3.74–3.82 (m, 2H), 4.01 (d, J=5 Hz, 2H), 5.50 (m, 1H), 6.84 (d, J=8 Hz, 2H), 7.23 (d, J=8 Hz, 2H).

Preparation 2

2-Amino-1-[4-(4-chlorophenyl)-1-piperazinyl]ethan-1-one dihydrochloride

To a solution of tert-butoxy-N-[2-[4-(4-chlorophenyl)-1-piperazinyl]-2-oxoethyl]formamide (31 g) in methanol (60 ml) was added 4N hydrogen chloride in ethyl acetate (219 ml) at 0° C. and the mixture was stirred at 0° C. for 30 minutes. The reaction mixture was allowed to warm to room temperature, stirred for 1 hour and diluted with ethyl acetate. The resulting solid was collected by filtration and washed with ethyl acetate. The solid was dried to give the title compound (29 g).

$^1$H-NMR (300 MHz, DMSO-d$_6$) δ 3.11–3.28 (m, 4H), 3.55 (m, 2H), 3.66 (m, 2H), 3.92 (m, 2H), 7.04 (d, J=9 Hz, 2H), 7.29 (d, J=9 Hz, 2H), 8.22 (br, 2H).

Preparation 3

(2S)-2-(tert-Butoxycarbonylamino)-N-[2-[4-(4-chlorophenyl)-1-piperazinyl]-2-oxoethyl]-3-(2-pyridyl)propanamide Diphenylphosphoryl azide (25 g) was added to a solution of (2S)-2-(tert-butoxycarbonylamino)-3-(2-pyridyl)propanoic acid (23 g) in N,N-dimethylformamide (230 ml) at 5° C. To the mixture was added a solid of 2-amino-1-[4-(4-chlorophenyl)-1-piperazinyl]-ethan-1-one dihydrochloride (28.2 g) at 5° C. with stirring and then diisopropylethylamine (47 ml) was added dropwise at 7–10° C. The mixture was stirred at 7–10° C. for 30 minutes and at room temperature for 2 hours. The mixture was diluted with saturated aqueous sodium hydrogencarbonate solution and extracted with ethyl acetate. The aqueous layer was extracted with two 500-ml portions of ethyl acetate, and the combined organic layers were extracted with 1N hydrochloric acid (150 ml×2). The combined aqueous layers were basified (pH 9) with sodium hydrogencarbonate and extracted with ethyl acetate. The organic layer was washed thoroughly with aqueous sodium hydrogencarbonate solution and brine, dried over magnesium sulfate and concentrated in vacuo to give the title compound (42 g).

$^1$H-NMR (300 MHz, CDCl$_3$) δ 1.44 (s, 9H), 3.11 (m, 4H), 3.23 (m, 1H), 3.34 (m, 1H), 3.53 (m, 2H), 3.75 (m, 2H), 4.04 (d, J=5 Hz, 2H), 4.64 (m, 1H), 6.38 (m, 1H), 6.83 (d, J=8 Hz, 2H), 7.10–7.27 (m, 4H), 7.59 (m, 1H), 7.77 (br, 1H), 8.52 (d, J=5 Hz, 1H).

Preparation 4

(2S)-2-Amino-N-[2-[4-(4-chlorophenyl)-1-piperazinyl]-2-oxoethyl]-3-(2-pyridyl)propanamide To a solution of (2S)-2-(tert-butoxycarbonylamino)-N-[2-[4-(4-chlorophenyl)-1-piperazinyl]-2-oxoethyl]-3-(2-pyridyl)-propanamide (42 g) in methanol (84 ml) was added 4N hydrogen chloride in ethyl acetate (209 ml) at 0° C. and the mixture was stirred at 0° C. for 30 minutes. The reaction mixture was allowed to warm to room temperature, stirred for 2 hours and diluted with ethyl acetate. The resulting solid was collected by filtration and washed with ethyl acetate. The solid was poured into aqueous sodium hydrogencarbonate solution and the mixture was extracted with chloroform. The aqueous layer was extracted twice with chloroform. The combined organic layers were dried over sodium sulfate and concentrated in vacuo to give a crude product of the title compound (27 g).

$^1$H-NMR (300 MHz, DMSO-d$_6$) δ 2.74 (dd, J=13 Hz,9 Hz, 1H), 3.06–3.23 (m, 5H), 3.50–3.70 (m, 5H), 3.93–4.12 (m, 2H), 6.97 (d, J=9 Hz, 2H), 7.17–7.34 (m, 4H), 7.70 (m, 1H), 8.24 (m, 1H), 8.49 (m, 1H).

EXAMPLE 1

5-Chloro-N-[(1S)-2-[[2-[4-(4-chlorophenyl)-1-piperazinyl]-2-oxoethyl]amino]-2-oxo-1-(2-pyridylmethyl)ethyl]-1-benzofuran-2-carboxamide To a suspension of (2S)-2-amino-N-[2-[4-(4-chlorophenyl)-1-piperazinyl]-2-oxoethyl]-3-(2-pyridyl)propanamide (18 g) and 5-chloro-1-benzofuran-2-carboxylic acid (8.8 g) in N,N-dimethyl-formamide (180 ml) were added 1-ethyl-3-(3-dimethylaminopropyl)-carbodiimide hydrochloride (9.44 g) and N-hydroxybenzotriazole (6.66 g) at 0° C. The mixture was stirred at room temperature for 14 hours. The reaction mixture was poured into ice-cold saturated aqueous sodium hydrogencarbonate solution and the resulting solid was collected by filtration. The solid was washed successively with saturated aqueous sodium hydrogencarbonate solution and water. The solid was crystallized from water:ethanol (1:9 (v/v)) to give the title compound (23 g) as crystals.

m.p. 172–173° C.

$^1$H-NMR (300 MHz, DMSO-d$_6$) δ 3.03–3.38 (m, 6H), 3.47–3.65 (m, 4H), 4.03 (m, 2H), 5.02 (m, 1H), 6.96 (d, J=9 Hz, 2H), 7.16–7.28 (m, 3H), 7.34 (d, J=9 Hz, 1H), 7.47–7.54 (m, 2H), 7.62–7.76 (m, 2H), 7.88 (s, 1H), 8.23 (dd, J=5 Hz,5 Hz, 1H), 8.49 (d, J=5 Hz, 1H), 9.03 (d, J=9 Hz, 1H).

EXAMPLE 2

(2E)-3-(4-Chlorophenyl)-N-[(1S)-2-[[2-[4-(4-chlorophenyl)-1-piperazinyl]-2-oxoethyl]amino]-2-oxo-1-(2-pyridylmethyl)ethyl]-2-propenamide To a suspension of (2S)-2-amino-N-[2-[4-(4-chlorophenyl)-1-piperazinyl]-2-oxoethyl]-3-(2-pyridyl)

propanamide (29 g) and 4-chlorocinnamic acid (13.1 g) in N,N-dimethylformamide (230 ml) were added 1-ethyl-3-(3-dimethylaminopropyl)carbodiimide hydrochloride (15.2 g) and N-hydroxybenzotriazole (10.7 g) at 0° C. The mixture was stirred at room temperature for 20 hours. The reaction mixture was poured into ice-cold saturated aqueous sodium hydrogencarbonate solution and the resulting solid was collected by filtration. The solid was washed successively with saturated aqueous sodium hydrogencarbonate solution and water. The solid was crystallized from water:ethanol (1:9 (v/v)) to give the title compound (34 g) as crystals.

m.p. 186–187° C.

$^1$H-NMR (300 MHz, CDCl$_3$) δ 3.06–3.16 (m, 4H), 3.26 (dd, J=13 Hz,6 Hz, 1H), 3.42 (dd, J=13 Hz,6 Hz, 1H), 3.48–3.56 (m, 2H), 3.71–3.79(m, 2H), 4.06 (d, J=6 Hz, 2H), 5.02 (m, 1H), 6.50 (d, J=15 Hz, 1H), 6.82 (d, J=8 Hz, 2H), 7.14–7.29 (m, 4H), 7.35 (d, J=8 Hz, 2H), 7.45 (d, J=8 Hz, 2H), 7.60 (d, J=15 Hz, 1H), 7.63 (m, 1H), 7.92 (d, J=7 Hz, 1H), 8.03 (m, 1H), 8.55 (m, 1H).

Preparation 5

Benzyl [[(2S)-2-[(tert-butoxycarbonyl)amino]-3-(2-pyridyl)propanoyl]amino]acetate To a solution of (2S)-2-[(tert-butoxycarbonyl)amino]-3-(2-pyridyl)propanoic acid (55.0 g), glycine benzyl ester tosylate (69.7 g), and diphenylphosphoryl azide (46.7 ml) in N,N-dimethylformamide (550 ml) was added dropwise N,N-diisopropylethylamine (75.6 ml) at 4° C. The mixture was warmed to room temperature and stirred for 3 hours. The resulting mixture was poured into ice-cold saturated aqueous sodium hydrogencarbonate solution (700 ml). The mixture was extracted twice with ethyl acetate (total 1.3 L) and washed successively with water (400 ml×2), saturated aqueous ammonium chloride solution (200 ml), aqueous sodium hydrogencarbonate solution (300 ml×2), and brine (40 ml). The organic layer was dried over anhydrous magnesium sulfate and concentrated to give the title compound (77.4 g) as pale brown crystals.

ESI-MS: 414.3(H+H)

$^1$H-NMR (300 MHz, CDCl$_3$) δ 8.48 (dd, J=5 Hz,2 Hz, 1H), 7.82 (br, 1H), 7.60 (td, J=8 Hz,2 Hz, 1H), 7.40–7.29 (m, 5H), 7.21 (d, J=8 Hz, 1H), 7.14 (dd, J=8 Hz,5 Hz, 1H), 6.33 (br, 1H), 5.15 (s, 2H), 4.62 (br, 1H), 4.04 (d, J=6 Hz, 2H), 3.36–3.18 (m, 2H), 1.43 (s, 9H).

Preparation 6

Benzyl [[(2S)-2-amino-3-(2-pyridyl)propanoyl]amino]acetate dihydrochloride

To a solution of benzyl [[(2S)-2-[(tert-butoxycarbonyl)amino]-3-(2-pyridyl)propanoyl]amino]acetate (73.8 g) in ethyl acetate (150 ml) was added dropwise 4N hydrogen chloride in ethyl acetate (669 ml) at 10° C. over 30 minutes. The mixture was warmed to room temperature and stirred for 3 hours. The mixture was diluted with ethyl acetate (300 ml). The resulting precipitate was collected by filtration, washed with ethyl acetate (700 ml), and dried in vacuo to give the title compound.

$^1$H-NMR (300 MHz, DMSO-d$_6$) δ 9.31 (t, J=6 Hz, 1H), 8.83 (d, J=5 Hz, 1H), 8.70 (br, 3H), 8.40 (t, J=8 Hz, 1H), 7.96 (d, J=8 Hz, 1H), 7.87 (t, J=5 Hz, 1H), 7.41–7.30 (m, 5H), 5.14 (s, 2H), 4.53 (br, 1H), 4.05 (dd, J=18 Hz,6 Hz, 1H), 3.99 (dd, J=18 Hz,6 HZ, 1H), 3.64 (dd, J=15 Hz,5 Hz, 1H), 3.54 (dd, J=15 Hz,8 Hz, 1H).

Preparation 7

Benzyl [[(2S)-2-[[(2E)-3-(4-chlorophenyl)-2-propenoyl]-amino]-3-(2-pyridyl)propanoyl]amino]acetate To a solution of 4-chlorocinnamic acid (49.2 g) in dichloromethane (400 ml) were added oxalyl chloride (30.5 ml) and 1 drop of N,N-dimethylformamide, and the mixture was stirred at room temperature for 6 hours. The reaction mixture was evaporated to dryness, and the residual acid chloride was dissolved in dichloromethane (900 ml). To this solution was added benzyl [[(2S)-2-amino-3-(2-pyridyl)propanoyl]amino]acetate dihydrochloride (104 g) at 10° C. followed by addition of triethylamine (116 ml) over 40 minutes. The mixture was allowed to warm to room temperature and stirred for 2 hours. The reaction mixture was evaporated to dryness, and the residue was washed successively with water (500 ml×5) and tetrahydrofuran-n-hexane (1:2, 500 ml×10), and dried in vacuo to give the title compound (115 g) as a white solid.

ESI-MS: 478.3(M+H)

$^1$H-NMR (300 MHz, CDCl$_3$) δ 8.51 (dd, J=5 Hz,2 Hz, 1H), 8.27 (t, J=5 Hz, 1H), 7.83 (d, J=6 Hz, 1H), 7.64 (td, J=8 Hz,2 Hz, 1H), 7.57 (d, J=16 Hz, 1H), 7.44 (d, J=9 Hz, 2H), 7.39–7.28 (m, 8H), 7.19 (dd, J=8 Hz,5 Hz, 1H), 6.47 (d, J=16 Hz, 1H), 5.14 (s, 2H), 4.98 (app q, J=6 Hz, 1H), 4.07 (d, J=5 Hz, 2H), 3.36 (dd, J=15 Hz,5 Hz, 1H), 3.26 (dd, J=15 Hz,6 Hz, 1H).

Preparation 8

[[(2S)-2-[[(2E)-3-(4-Chlorophenyl)-2-propenoyl]amino]-3-(2-pyridyl)propanoyl]amino]acetic acid To a suspension of benzyl [[(2S)-2-[[(2E)-3-(4-chlorophenyl)-2-propenoyl]amino]-3-(2-pyridyl)propanoyl]amino]-acetate (10.8 g) in methanol (200 ml) was added 1N aqueous sodium hydroxide solution (22.6 ml), and the mixture was stirred at room temperature for 5 hours. The reaction mixture was concentrated in vacuo, and the residue was treated with aqueous citric acid solution (10%, 100 ml). The resulting white precipitate was collected by filtration, washed with tetrahydrofuran-hexane (1:1, 150 ml), and dried in vacuo to give the title compound (8.25 g) as a white solid.

ESI-MS: 388.2(M+H)

$^1$H-NMR (300 MHz, DMSO-d$_6$) δ 12.6 (br, 1H), 8.50–8.36 (m, 3H), 7.68 (td, J=8 Hz,2 Hz, 1H), 7.56 (d, J=9 Hz, 2H), 7.47 (d, J=9 Hz, 2H), 7.34 (d, J=16 Hz, 1H), 7.30 (d, J=8 Hz, 1H), 7.20 (dd, J=8 Hz,5 Hz, 1H), 6.68(d, J=16 Hz, 1H), 4.96–4.86 (m, 1H), 3.78 (dd, J=18 Hz,6 Hz, 1H), 3.74(dd, J=18 Hz,6 Hz, 1H), 3.24(dd, J=14 Hz,5 Hz, 1H), 2.99(dd, J=14 Hz,10 Hz, 1H).

Preparation 9

Benzyl [[(2S)-2-[[(5-chloro-1-benzofuran-2-yl)carbonyl]-amino]-3-(2-pyridyl)propanoyl]amino]acetate The title compound was obtained from benzyl [[(2S)-2-amino-3-(2-pyridyl)propanoyl]amino]acetate dihydrochloride and 5-chloro-1-benzofuran-2-carboxylic acid in substantially the same manner as in Preparation 7.

ESI-MS: 492.3(M+H)

$^1$H-NMR (300 MHz, CDCl$_3$) δ 8.70–8.49 (m, 3H), 7.71–7.62 (m, 2H), 7.52–7.18 (m, 10H), 5.16 (s, 2H), 5.11–5.02 (m, 1H), 4.19–4.03 (m, 2H), 3.44 (dd, J=15 Hz,4 Hz, 1H), 3.35 (dd, J=15 Hz,7 Hz, 1H).

Preparation 10

[[(2S)-2-[[(5-Chloro-1-benzofuran-2-yl)carbonyl]amino]-3-(2-pyridyl)propanoyl]amino]acetic acid The title compound was obtained from benzyl [[(2S)-2-[[(5-chloro-1-benzofuran-2-yl)carbonyl]amino]-3-(2-pyridyl)propanoyl]-amino]acetate in substantially the same manner as in Preparation 8.

ESI-MS: 402.2(M+H)

$^1$H-NMR (300 MHz, DMSO-d$_6$) δ 12.6 (br, 1H), 9.00 (d, J=8 Hz, 1H), 8.49 (dd, J=5 Hz,2 Hz, 1H), 8.46 (t, J=6 Hz, 1H), 7.88 (d, J=2 Hz, 1H), 7.72 (d, J=9 Hz, 1H), 7.67 (td, J=8 Hz,2 Hz, 1H), 7.53(d, J=1 Hz, 1H), 7.48(dd, J=9 Hz,2 Hz, 1H), 7.33 (d, J=8 Hz, 1H), 7.20 (dd, J=8 Hz,5 Hz, 1H), 5.04–4.94 (m, 1H), 3.80 (dd, J=18 Hz,6 Hz, 1H), 3.74 (dd, J=18 Hz,6 Hz, 1H), 3.32 (dd, J=14 Hz,4 Hz, 1H), 3.22 (dd, J=14 Hz,10 Hz, 1H).

Preparation 11

(S)-1-Phenyl-3-methylpiperazine

A mixture of bromobenzene (300 mg), (S)-2-methylpiperazine (230 mg), (S)-(-)-2,2'-bis(diphenylphosphino)-1,1'-binaphthyl (BINAP) (48 mg), sodium tert-butoxide (266 mg), tris-(dibenzylideneacetone)dipalladium(0) (26 mg) and toluene (15 ml) was stirred at 100° C. for 4 hours under a nitrogen atmosphere. The mixture was cooled to room temperature and saturated aqueous sodium hydrogencarbonate solution was added thereto. The organic layer was separated, washed with brine and dried over magnesium sulfate. The solvent was removed under reduced pressure. The obtained crude product was purified by silica gel column chromatography (chloroform-methanol 20:1) to give the title compound in a pure form.

$^1$H-NMR (300 MHz, CDCl$_3$) δ 1.11 (d, J=6 Hz, 3H), 2.37 (dd, J=12 Hz,1 Hz, 1H), 2.72 (td, J=12 Hz,3 Hz, 1H), 2.95–3.18 (m, 3H), 3.52 (d, J=12 Hz, 2H), 6.82–6.98 (m, 3H), 7.22–7.29 (m,2H).

EXAMPLE 3

5-Chloro-N-[(1S)-2-[[2-((2S)-2-methyl-4-phenyl-1-piperazinyl)-2-oxoethyl]amino]-2-oxo-1-(2-pyridylmethyl)ethyl]-1-benzofuran-2-carboxamide A mixture of [[(2S)-2-[[(5-chloro-1-benzofuran-2-yl)carbonyl]amino]-3-(2-pyridyl)propanoyl]amino]acetic acid (150 mg), (S)-1-phenyl-3-methylpiperazine (79 mg), 1-hydroxy-benzotriazole (55 mg) and 1-(3-dimethylaminopropyl)-3-ethylcarbodiimide (79 mg) in N,N-dimethylformamide (3 ml) was stirred at room temperature for 18 hours. The reaction mixture was diluted with ethyl acetate (15 ml), and washed successively with saturated aqueous sodium hydrogencarbonate solution, water, and brine. The organic layer was dried over magnesium sulfate, and the solvent was removed under reduced pressure. The residue was purified by silica gel column chromatography (chloroform-methanol 10:1) to give the title compound as a colorless amorphous solid.

$^1$H-NMR (300 MHz, CDCl$_3$) δ 1.35 (dd, J=4 Hz,18 Hz, 3H), 2.62–2.96 (m, 2H), 3.07–3.21 (m, 1H), 3.34 (dd, J=5 Hz,14 Hz, 1H), 3.36–3.59 (m, 4H), 3.49 (dd, J=5 Hz,14 Hz, 1H), 3.94–4.26 (m, 2H), 4.44 (br, 1H), 5.12 (td, J=6 Hz,6 Hz, 1H), 6.86–6.94 (m, 2H), 7.16–7.30 (m, 4H), 7.36–7.51 (m, 3H), 7.60–7.68 (m, 2H), 8.18 (br, 1H), 8.62 (d, J=3 Hz, 1H), 8.78 (br, 1H).

EXAMPLE 4

(2E)-3-(4-Chlorophenyl)-N-[(1S)-2-[[2-((2S)-2-methyl-4-phenyl-1-piperazinyl)-2-oxoethyl]amino]-2-oxo-1-(2-pyridyl-methyl)ethyl]-2-propenamide The title compound was obtained from (S)-1-phenyl-3-methylpiperazine and [[(2S)-2-[[(2E)-3-(4-chlorophenyl)-2-propenoyl]amino]-3-(2-pyridyl)propanoyl]amino]acetic acid in substantially the same manner as in Example 3.

$^1$H-NMR (300 MHz, CDCl$_3$) δ 1.37 (dd, J=4 Hz,18 Hz, 3H), 2.62–2.78 (m, 1H), 2.89 (br, 1H), 3.07–3.21 (m, 1H), 3.26 (dd, J=5 Hz,14 Hz, 1H), 3.37–3.58 (m, 4H), 3.46 (dd, J=5 Hz,14 Hz, 1H), 3.90–4.21 (m, 2H), 4.42 (br, 1H), 5.12 (td, J=6 Hz,6 Hz, 1H), 6.49 (d, J=10 Hz, 1H), 6.85–6.92 (m, 3H), 7.14–7.20 (m, 1H), 7.22–7.48 (m, 5H), 7.42–7.49 (m, 2H), 7.56–7.67 (m, 2H), 7.89–8.09 (m, 3H), 8.55 (d, J=3 Hz, 1H).

Preparation 12

(3R,5S)-1-(4-Chlorophenyl)-3,5-dimethylpiperazine

A mixture of 4-bromochlorobenzene (1.0 g), cis-2,6-dimethylpiperazine (716 mg), sodium tert-butoxide (728 mg), (S)-(-)-BINAP (97.6 mg), and tris(dibenzylideneacetone)dipalladium(0) (71.6 mg) in anhydrous toluene (50 ml) was heated at 100° C. under a nitrogen atmosphere for 3 hours. The dark colored reaction mixture was filtered through celite and the celite was washed with chloroform. The filtrate was concentrated, and the residue was purified by silica gel column chromatography (chloroform-methanol 60:1) to give the title compound as a yellow powder (1.15 g).

ESI-MS: 225.2(M+H)

$^1$H-NMR (300 MHz, CDCl$_3$) δ 7.19 (d, J=9 Hz, 2H), 6.84 (d, J=9 Hz, 21), 3.46 (m, 2H), 3.08–2.97 (m, 2H), 2.27 (dd, J=11 Hz,11 Hz, 2H), 1.50 (br s, 1H), 1.14 (d, J=6 Hz, 6H).

EXAMPLE 5

5-Chloro-N-[(1S)-2-[[2-[(2R,6S)-4-(4-chlorophenyl)-2,6-dimethyl-1-piperazinyl]-2-oxoethyl]amino]-2-oxo-1-(2-pyridylmethyl)ethyl]-1-benzofuran-2-carboxamide The title compound was obtained from (3R,5S)-1-(4-chlorophenyl)-3,5-dimethylpiperazine and [[(2S)-2-[[(5-chloro-1-benzofuran-2-yl)carbonyl]amino]-3-(2-pyridyl)propanoyl]-amino]acetic acid in substantially the same manner as in Example 3.

ESI-MS: 608.2(M+H)

$^1$H-NMR (300 MHz, CDCl$_3$) δ 8.87–8.73 (br, 1H), 8.66–8.60 (m, 1H), 8.24–8.07 (br m, 1H), 7.69–7.62 (m, 2H), 7.49(d, J=9 Hz, 1H), 7.43(s, 1H), 7.39(dd, J=9 Hz,2 Hz, 1H), 7.31–7.18 (m, 4H), 6.83(d, J=9 Hz, 2H), 5.16–5.08 (m, 1H), 4.71–4.57 (br, 1H), 4.25–4.85 (m, 3H), 3.50 (dd, J=15 Hz,5 Hz, 1H), 3.39–3.30 (m, 3H), 2.92–2.77 (br m, 2H), 1.51–1.30 (br m, 6H).

Preparation 13

(3R,5S)-3,5-Dimethyl-1-(4-methylphenyl)piperazine

The title compound was obtained from 4-bromotoluene and cis-2,6-dimethylpiperazine in substantially the same manner as in Preparation 12.

ESI-MS: 205.2(M+H)

$^1$H-NMR (300 MHz, CDCl$_3$) δ 7.07 (d, J=9 Hz, 2H), 6.85 (d, J=9 Hz, 2H), 3.49–3.42 (m, 2H), 3.11–2.99 (m, 2H), 2.27 (s, 3H), 2.25 (dd, J=11 Hz,11 Hz, 2H), 1.55 (br s, 1H), 1.13 (d, J=6 Hz, 6H).

EXAMPLE 6

(2E)-3-(4-Chlorophenyl)-N-[(1S)-2-[[2-[(2R,6S)-2,6-dimethyl-4-(4-methylphenyl)-1-piperazinyl]-2-oxoethyl]amino]-2-oxo-1-(2-pyridylmethyl)ethyl]-2-propenamide The title compound was obtained from (3R,5S)-3,5-dimethyl-1-(4-methylphenyl)piperazine and [[(2S)-2-[[(2E)-3-(4-chlorophenyl)-2-propenoyl]amino]-3-(2-pyridyl)propanoyl]amino]-acetic acid in substantially the same manner as in Example 3.

ESI-MS: 574.4(M+H)

$^1$H-NMR (300 MHz, CDCl$_3$) δ 8.60–8.53 (br m, 1H), 8.03–7.87 (br, 2H), 7.63 (td, J=8, 2 Hz, 1H), 7.61 (d, J=16 Hz, 1H), 7.46 (d, J=8 Hz, 2H), 7.35 (d, J=8 Hz, 2H), 7.26 (d, J=8 Hz, 1H), 7.18 (dd, J=8 Hz,5 Hz, 1H), 7.09 (d, J=8 Hz, 2H), 6.83 (d, J=8 Hz, 2H), 6.50 (d, J=16 Hz, 1H), 5.07–4.99 (m, 1H), 4.70–4.57 (br, 1H), 4.22–3.80 (br m, 3H), 3.44 (dd, J=15 Hz,5 Hz, 1H), 3.35 (app s, 1H), 3.31 (app s, 1H), 3.27 (dd, J=15 Hz,5 Hz, 1H), 2.87–2.75 (br m, 2H), 2.28 (s, 3H), 1.50–1.32 (br m, 6H).

Preparation 14

3-Methyl-1-(4-methylphenyl)piperazine

The title compound was obtained from 4-bromotoluene and 2-methylpiperazine in substantially the same manner as in Preparation 12.

ESI-MS: 191.2(M+H)

$^1$H-NMR (300 MHz, CDCl$_3$) δ 7.07 (d, J=8 Hz, 2H), 6.85 (d, J=8 Hz, 2H), 3.49–3.41 (m, 2H), 3.15–2.92 (m, 3H), 2.66 (td, J=12 Hz,4 Hz, 1H), 2.35–2.24 (m, 1H), 2.27 (s, 3H), 1.66 (br s, 1H), 1.12 (d, J=7 Hz, 3H).

EXAMPLE 7

(2E)-3-(4-Chlorophenyl)-N-[(1S)-2-[[2-[2-methyl-4-(4-methylphenyl)-1-piperazinyl]-2-oxoethyl]amino]-2-oxo-1-(2-pyridylmethyl)ethyl]-2-propenamide The title compound was obtained from 3-methyl-1-(4-methylphenyl)piperazine and [[(2S)-2-[[(2E)-3-(4-chlorophenyl)-2-propenoyl]amino]-3-(2-pyridyl)propanoyl]amino]acetic acid in substantially the same manner as in Example 3.

$^1$H-NMR (300 MHz, CDCl$_3$, a mixture of diastereomers) δ 8.58–8.54 (m, 1H), 8.10–7.89 (m, 2H), 7.63 (td, J=8, 2 Hz, 1H), 7.61(d, J=16 Hz, 1H), 7.45 (d, J=8 Hz, 2H), 7.35 (d, J=8 Hz, 2H), 7.26 (d, J=8 Hz, 1H), 7.18 (dd, J=8 Hz,5 Hz, 1H), 7.08 (d, J=8 Hz, 2H), 6.80 (d, J=8 Hz, 2H), 6.50 (d, J=16 Hz, 1H), 5.06–4.98 (m, 1H), 4.82–4.72 (br, 0.5H), 4.47–4.38 (br m, 0.5H), 4.22–3.87 (br m, 2H), 3.58–3.06 (m, 6H), 2.89–2.56 (br m, 2H), 2.27 (s, 3H), 1.44–1.21 (m, 3H).

Preparation 15

(3S)-1-(4-Chlorophenyl)-3-methylpiperazine

The title compound was obtained from 4-bromochlorobenzene and (S)-(+)-2-methylpiperazine in substantially the same manner as in Preparation 12.

ESI-MS: 211.3(M+H)

$^1$H-NMR (300 MHz, CDCl$_3$) δ 7.20 (d, J=9 Hz, 2H), 6.84 (d, J=9 Hz, 2H), 3.50–3.42 (m, 2H), 3.15–2.91 (m, 3H), 2.68 (td, J=12 Hz,4 Hz, 1H), 2.33 (dd, J=12 Hz,10 Hz, 1H), 1.58 (br s, 1H), 1.13 (d, J=6 Hz, 3H).

EXAMPLE 8

5-Chloro-N-[(1S)-2-[[2-[(2S)-4-(4-chlorophenyl)-2-methyl-1-piperazinyl]-2-oxoethyl]amino]-2-oxo-1-(2-pyridylmethyl)ethyl]-1-benzofuran-2-carboxamide The title compound was obtained from (3S)-1-(4-chlorophenyl)-3-methylpiperazine and [[(2S)-2-[[(5-chloro-1-benzofuran-2-yl)carbonyl]amino]-3-(2-pyridyl)propanoyl]amino]acetic acid in substantially the same manner as in Example 3.

ESI-MS: 594.8(M+H)

$^1$H-NMR (300 MHz, CDCl$_3$) δ 8.82–8.75 (m, 1H), 8.62 (dd, J=5,2 Hz, 1H), 8.28–8.10 (br m, 1H), 7.65 (td, J=8 Hz,2 Hz, 1H), 7.65 (d, J=2 Hz, 1H), 7.49 (dd, J=9 Hz,1 Hz, 1H), 7.42 (d, J=1 Hz, 1H), 7.38 (dd, J=9 Hz,2 Hz, 1H), 7.30–7.17 (m, 4H), 6.80 (d, J=9 Hz, 2H), 5.15–5.08 (m, 1H), 4.84–4.71 (br, 0.5H), 4.48–4.37 (br m, 0.5H), 4.26–3.91 (m, 2H), 3.60–3.41 (m, 3H), 3.40–3.28 (m, 2H), 3.20–2.60 (br m, 3H), 1.44–1.22 (m, 3H).

EXAMPLE 9

5-Chloro-N-[(1S)-2-[[2-[4-(2,4-difluorophenyl)-1-piperazinyl]-2-oxoethyl]amino]-2-oxo-1-(2-pyridylmethyl)ethyl]-1-benzofuran-2-carboxamide The title compound was obtained from 1-(2,4-difluorophenyl)piperazine and [[(2S)-2-[[(5-chloro-1-benzofuran-2-yl)carbonyl]amino]-3-(2-pyridyl)propanoyl]amino]acetic acid in substantially the same manner as in Example 3.

ESI-MS: 582.2(M+H)

$^1$H-NMR (300 MHz, CDCl$_3$) δ 8.76 (d, J=7 Hz, 1H), 8.62 (dd, J=5 Hz,2 Hz, 1H), 8.19 (t, J=4 Hz, 1H), 7.65 (d, J=2 Hz, 1H), 7.65 (td, J=8 Hz,2 Hz, 1H), 7.49 (dd, J=9 Hz,1 Hz, 1H), 7.42 (d, J=1 Hz, 1H), 7.39 (dd, J=9 Hz,2 Hz, 1H), 7.28 (d, J=8 Hz, 1H), 7.20 (dd, J=8 Hz,5 Hz, 1H), 6.91–6.76 (m, 3H), 5.16–7.08 (m, 1H), 4.09 (d, J=4 Hz, 2H), 3.83–3.69 (m, 2H), 3.58–3.51 (m, 2H), 3.49 (dd, J=15 Hz,5 Hz, 1H), 3.34 (dd, J=15 Hz,6 Hz, 1H), 3.03–2.93 (m, 4H).

EXAMPLE 10

(2E)-3-(4-Chlorophenyl)-N-[(1S)-2-oxo-2-[[2-oxo-2-[4-[5-(trifluoromethyl)-2-pyridyl]-1-piperazinyl]ethyl]amino]-1-(2-pyridylmethyl)ethyl]-2-propenamide The title compound was obtained from 1-[5-(trifluoromethyl)-2-pyridyl]piperazine and [[(2S)-2-[[(2E)-3-(4-chlorophenyl)-2-propenoyl]amino]-3-(2-pyridyl)propanoyl]amino]-acetic acid in substantially the same manner as in Example 3.

ESI-MS: 601.3(M+H)

$^1$H-NMR (300 MHz, CDCl$_3$) δ 8.56 (dd, J=5 Hz,2 Hz, 1H), 8.42–8.39 (brm, 1H), 8.06 (t, J=4 Hz, 1H), 7.92 (d, J=7 Hz, 1H), 7.70–7.57 (m, 3H), 7.46 (d, J=9 Hz, 2H), 7.35 (d, J=9 Hz, 2H), 7.27 (d, J=8 Hz, 1H), 7.19 (dd, J=8 Hz,5 Hz, 1H), 6.64 (d, J=9 Hz, 1H), 6.50 (d, J=15 Hz, 1H), 5.06–4.98 (m, 1H), 4.08 (d, J=4 Hz, 1H), 3.77–3.67 (m, 4H), 3.66–3.59 (m, 2H), 3.54–3.48 (m, 2H), 3.43 (dd, J=15 Hz,5 Hz, 1H), 3.27 (dd, 15 Hz,5 Hz, 1H).

EXAMPLE 11

5-Chloro-N-[(1S)-2-oxo-2-[[2-oxo-2-[4-[5-(trifluoromethyl)-2-pyridyl]-1-piperazinyl]ethyl]amino]-1-(2-pyridylmethyl)ethyl]-1-benzofuran-2-carboxamide The title compound was obtained from 1-[5-(trifluoromethyl)-2-pyridyl]piperazine and [[(2S)-2-[[(5-chloro-1-benzofuran-2-yl)carbonyl]amino]-3-(2-pyridyl)propanoyl]-amino]acetic acid in substantially the same manner as in Example 3.

ESI-MS: 615.3(M+H)

$^1$H-NMR (300 MHz, CDCl$_3$) δ 8.76 (d, J=7 Hz, 1H), 8.62 (dd, J=5,2 Hz, 1H), 8.43–8.39 (brm, 1H), 8.22 (t, J=4 Hz, 1H), 7.70–7.61 (m, 3H), 7.49 (dd, J=9,1 Hz, 1H), 7.42 (d, J=1 Hz, 1H), 7.39 (dd, J=9 Hz,2 Hz, 1H), 7.28 (d, J=8 Hz, 1H), 7.21 (dd, J=8 Hz,5 Hz, 1H), 6.64 (d, J=9 Hz, 1H), 5.16–5.08 (m, 1H), 4.11 (d, J=4 Hz, 2H), 3.77–3.69 (m, 4H), 3.66–3.59 (m, 2H), 3.55–3.44 (m, 3H), 3.35 (dd, J=15 Hz,6 Hz, 1H).

EXAMPLE 12

(2E)-3-(4-Chlorophenyl)-N-[(1S)-2-[[2-[4-(5-chloro-2-pyridyl)-1-piperazinyl]-2-oxoethyl]amino]-2-oxo-1-(2-pyridylmethyl)ethyl]-2-propenamide The title compound was obtained from 1-(5-chloro-2-pyridyl)piperazine and [[(2S)-2-[[(2E)-3-(4-chlorophenyl)-2-propenoyl]amino]-3-(2-pyridyl)propanoyl]amino]acetic acid in substantially the same manner as in Example 3.

ESI-MS: 567.3(M+H)

$^1$H-NMR (300 MHz, CDCl$_3$) δ 8.56 (dd, J=5 Hz,2 Hz, 1H), 8.12 (d, J=3 Hz, 1H), 8.06 (t, J=4 Hz, 1H), 7.92 (d, J=7 Hz, 1H), 7.63 (td, J=8 Hz,2 Hz, 1H), 7.61 (d, J=15 Hz, 1H), 7.49–7.42 (m, 3H), 7.35 (d, J=9 Hz, 2H), 7.29–7.24 (m, 1H), 7.18 (dd, J=8 Hz,5 Hz, 1H), 6.58 (d, J=9 Hz, 1H), 6.50 (d, J=15 Hz, 1H), 5.05–4.98 (m, 1H), 4.07 (d, J=4 Hz, 2H), 3.77–3.65 (br m, 2H), 3.60–3.37 (m, 7H), 3.26 (dd, J=15 Hz,5 Hz, 1H).

EXAMPLE 13

5-Chloro-N-[(1S)-2-[[2-[4-(5-chloro-2-pyridyl)-1-piperazinyl]-2-oxoethyl]amino]-2-oxo-1-(2-pyridylmethyl)ethyl]-1-benzofuran-2-carboxamide The title compound was obtained from 1-(5-chloro-2-pyridyl)piperazine and [[(2S)-2-[[(5-chloro-1-benzofuran-2-yl)carbonyl]amino]-3-(2-pyridyl)propanoyl]amino]acetic acid in substantially the same manner as in Example 3.

ESI-MS: 581.1(M+H)]

$^1$H-NMR (300 MHz, DMSO-d$_6$) δ 9.04 (d, J=8 Hz, 1H), 8.49 (dd, J=5 Hz,2 Hz, 1H), 8.22 (t, J=5 Hz, 1H), 8.12 (d, J=3 Hz, 1H), 7.87 (d, J=2 Hz, 1H), 7.71 (d, J=9 Hz, 1H), 7.68 (td, J=8 Hz,2 Hz, 1H), 7.62 (dd, J=9 Hz,3 Hz, 1H), 7.54 (d, J=1 Hz, 1H), 7.49 (dd, J=9 Hz,2 Hz, 1H), 7.34 (d, J=8 Hz, 1H), 7.20 (dd, J=8 Hz,5 Hz, 1H), 6.89 (d, J=9 Hz, 1H), 5.08–4.96 (m, 1H), 4.05 (dd, J=16 Hz,5 Hz, 1H), 4.01 (dd, J=16 Hz,5 Hz, 1H), 3.60–3.43 (br m, 8H), 3.37–3.18 (m, 2H).

Preparation 16

1-(1,3-Thiazol-2-yl)piperazine

The title compound was obtained from 2-bromothiazole and piperazine in substantially the same manner as in Preparation 12.

ESI-MS: 170.0(M+H)

$^1$H-NMR (300 MHz, CDCl$_3$) δ 7.20 (d, J=4 Hz, 1H), 6.57 (d, J=4 Hz, 1H), 3.48–3.43 (m, 4H), 3.02–2.96 (m, 4H), 1.71 (br s, 1H).

EXAMPLE 14

5-Chloro-N-[(1S)-2-oxo-2-[[2-oxo-2-[4-(1,3-thiazol-2-yl)-1-piperazinyl]ethyl]amino]-1-(2-pyridylmethyl)ethyl]-1-benzofuran-2-carboxamide The title compound was obtained from 1-(1,3-thiazol-2-yl)piperazine and [[(2S)-2-[[(5-chloro-1-benzofuran-2-yl)carbonyl]amino]-3-(2-pyridyl)propanoyl]amino]acetic acid in substantially the same manner as in Example 3.

ESI-MS: 553.2(M+H)

$^1$H-NMR (300 MHz, CDCl$_3$) δ 8.77 (d, J=7 Hz, 1H), 8.63 (dd, J=5 Hz,2 Hz, 1H), 8.28–8.21 (br m, 1H), 7.69–7.62 (m, 3H), 7.50 (dd, J=9 Hz,1 Hz, 1H), 7.43 (d, J=1 Hz, 1H), 7.40 (dd, J=9 Hz,2 Hz, 1H), 7.29 (d, J=8 Hz, 1H), 7.24–7.18 (m, 2H), 6.65 (d, J=4 Hz, 1H), 5.16–5.08 (m, 1H), 4.11 (d, J=4 Hz, 1H), 3.78–3.72 (m, 2H), 3.56–3.43 (m, 7H), 3.35 (dd, J=15 Hz,6 Hz, 1H).

Preparation 17

1-(5-Chloro-2-thienyl)piperazine

The title compound was obtained from 2-bromo-5-chlorothiophene and piperazine in substantially the same manner as in Preparation 12.

ESI-MS: 203.0(M+H)

$^1$H-NMR (300 MHz, CDCl$_3$) δ 6.58 (d, J=4 Hz, 1H), 5.88 (d, J=4 Hz, 1H), 3.20–2.80 (m, 8H), 1.71 (br s, 1H).

EXAMPLE 15

5-Chloro-N-[(1S)-2-[[2-[4-(5-chloro-2-thienyl)-1-piperazinyl]-2-oxoethyl]amino]-2-oxo-1-(2-pyridylmethyl)ethyl]-1-benzofuran-2-carboxamide The title compound was obtained from 1-(5-chloro-2-thienyl)piperazine and [[(2S)-2-[[(5-chloro-1-benzofuran-2-yl)carbonyl]amino]-3-(2-pyridyl)propanoyl]amino]acetic acid in substantially the same manner as in Example 3.

ESI-MS: 586.2(M+H)

$^1$H-NMR (300 MHz, CDCl$_3$) δ 8.75 (d, J=7 Hz, 1H), 8.61 (dd, J=5 Hz,2 Hz, 1H), 8.24–8.17 (br m, 1H), 7.65 (td, J=8 Hz,2 Hz, 1H), 7.65 (d, J=2 Hz, 1H), 7.49 (dd, J=9 Hz,1 Hz, 1H), 7.42 (d, J=1 Hz, 1H), 7.39 (dd, J=9 Hz,2 Hz, 1H), 7.28 (d, J=8 Hz, 1H), 7.21 (dd, J=8 Hz,5 Hz, 1H), 6.58 (d, J=4 Hz, 1H), 5.96 (d, J=4 Hz, 1H), 5.15–5.07 (m, 1H), 4.08 (d. J=4 Hz, 2H), 3.76–3.69 (m, 2H), 3.55–3.43 (m, 3H), 3.34 (dd, J=15 Hz,6 Hz, 1H), 3.07–2.98 (m, 4H).

EXAMPLE 16

(2E)-3-(4-Chlorophenyl)-N-[(1S)-2-[[2-[4-(5-chloro-2-thienyl)-1-piperazinyl]-2-oxoethyl]amino]-2-oxo-1-(2-pyridylmethyl)ethyl]-2-propenamide The title compound was obtained from 1-(5-chloro-2-thienyl)piperazine and [[(2S)-2-[[(2E)-3-(4-chlorophenyl)-2-propenoyl]amino]-3-(2-pyridyl)propanoyl]amino]acetic acid in substantially the same manner as in Example 3.

ESI-MS: 572.2(M+H)

$^1$H-NMR (300 MHz, CDCl$_3$) δ 8.55 (dd, J=5 Hz,2 Hz, 1H), 8.06–8.00 (br m, 1H), 7.91 (d, J=4 Hz, 1H), 7.63 (td, J=8 Hz,2 Hz, 1H), 7.60 (d, J=15 Hz, 1H), 7.46 (d, J=9 Hz, 2H), 7.35 (d, J=9 Hz, 2H), 7.29–7.24 (m, 1H), 7.18 (dd, J=8 Hz,5 Hz, 1H), 6.58 (d, J=4 Hz, 1H), 6.49 (d, J=15 Hz, 1H), 5.96 (d, J=4 Hz, 1H), 5.05–4.97 (m, 1H), 4.05 (d, J=4 Hz, 1H), 3.76–3.69 (m, 2H), 3.53–3.47 (m, 2H), 3.42 (dd, J=15 Hz,5 Hz, 1H), 3.26 (dd, J=15 Hz,6 Hz, 1H), 3.06–2.98 (m, 4H).

Preparation 18

1-(2-Thienyl)piperazine

The title compound was obtained from 2-bromothiophene and piperazine in substantially the same manner as in Preparation 12.

ESI-MS: 169.0(M+H)

$^1$H-NMR (300 MHz, CDCl$_3$) δ 6.79 (dd, J=5 Hz,4 Hz, 1H), 6.61 (dd, J=5 Hz,1 Hz, 1H), 6.13 (dd, J=4 Hz,1 Hz, 1H), 3.13–3.09 (m, 4H), 3.04–3.00 (m, 4H), 1.64 (br s, 1H).

EXAMPLE 17

(2E)-3-(4-Chlorophenyl)-N-[(1S)-2-oxo-2-[[2-oxo-2-[4-(2-thienyl)-1-piperazinyl]ethyl]amino]-1-(2-pyridylmethyl)ethyl]-2-propenamide The title compound was obtained from 1-(2-thienyl)-piperazine and [[(2S)-2-[[(2E)-3-(4-chlorophenyl)-2-propenoyl]amino]-3-(2-pyridyl)propanoyl]amino]acetic acid in substantially the same manner as in Example 3.

ESI-MS: 538.2(M+H)

$^1$H-NMR (300 MHz, CDCl$_3$) δ 8.55 (dd, J=5 Hz,2 Hz, 1H), 8.04 (t, J=4 Hz, 1H), 7.93 (d, J=7 Hz, 1H), 7.64 (td, J=8 Hz,2 Hz, 1H), 7.61 (d, J=16 Hz, 1H), 7.46 (d, J=9 Hz, 2H), 7.35 (d, J=9 Hz, 2H), 7.26 (d, J=8 Hz, 1H), 7.19 (dd, J=8 Hz,5 Hz, 1H), 6.79 (dd, J=5 Hz,4 Hz, 1H), 6.69 (dd, J=5 Hz,1 Hz, 1H), 6.50 (d, J=16 Hz, 1H), 6.19 (dd, J=4 Hz,1 Hz, 1H), 5.07–4.98 (m, 1H), 4.06 (d, J=4 Hz, 2H), 3.79–3.70 (m, 2H), 3.56–3.48 (m, 2H), 3.43 (dd, J=15 Hz,5 Hz, 1H), 3.27 (dd, J=15 Hz,5 Hz, 1H), 3.10 (br s, 4H).

EXAMPLE 18

5-Chloro-N-[(1S)-2-oxo-2-[[2-oxo-2-[4-(2-thienyl)-1-piperazinyl]ethyl]amino]-1-(2-pyridylmethyl)ethyl]-1-benzofuran-2-carboxamide The title compound was obtained from 1-(2-thienyl)piperazine and [[(2S)-2-[[(5-chloro-1-benzofuran-2-yl)carbonyl]amino]-3-(2-pyridyl)propanoyl]amino]acetic acid in substantially the same manner as in Example 3.

m.p. 75–85° C.

MS(ES+): 552.32

¹H-NMR (300 MHz, CDCl₃) δ 3.06–3.13 (m, 4H), 3.30–3.56 (m, 4H), 3.72–3.77 (m, 2H), 4.07–4.09 (m, 2H), 5.07–5.15 (m, 1H), 6.16 (m, 1H,), 6.67 (d, J=7.5 Hz, 1H), 6.77 (d, J=7.5 Hz, 1H), 7.15–7.67 (m, 7H), 8.20 (br s, 11), 8.58 (d, J=6 Hz, 1H), 8.75 (d, J=7.5 Hz, 1H).

Preparation 19 tert-Butyl 4-(3,3,3-trifluoropropyl)-1-piperazine-carboxylate

To a solution of 1-(tert-butoxycarbonyl)piperazine (5.00 g) and N,N-diisopropylethylamine (4.68 ml) in N,N-dimethylformamide (13 ml) was added 1-bromo-3,3,3-trifluoropropane (5.00 ml) at 60° C. The mixture was stirred at 60° C. for 4 hours. The reaction mixture was poured into saturated aqueous sodium hydrogencarbonate solution and extracted with hexane. The organic layer was washed successively with saturated aqueous ammonium chloride solution, aqueous sodium hydrogencarbonate solution and brine, dried over anhydrous magnesium sulfate and concentrated to give the title compound (5.38 g) as a pale yellow solid.

ESI-MS: 283.2(M+H)

¹H-NMR (300 MHz, CDCl₃) δ 3.44 (t, J=5 Hz, 4H), 2.57–2.65 (m, 2H), 2.40 (t, J=5 Hz, 4H), 2.37–2.23 (m, 2H), 1.46 (s, 9H).

Preparation 20

1-(3,3,3-Trifluoropropyl)piperazine dihydrochloride

To a solution of tert-butyl 4-(3,3,3-trifluoropropyl)-1-piperazinecarboxylate (5.77 g) in ethyl acetate (13 ml) and methanol (10 ml) was added dropwise 4N hydrogen chloride in ethyl acetate (29 ml) at 0° C. The mixture was warmed to room temperature and stirred for 2 hours. The reaction mixture was diluted with ethyl acetate. The resulting precipitate was collected by filtration, washed with ethyl acetate and dried in vacuo to give the title compound (4.70 g) as a pale yellow solid.

¹H-NMR (300 MHz, DMSO-d₆) δ 9.89 (br s, 2H), 3.43 (br s, 10H), 3.02–2.86 (m, 2H).

EXAMPLE 19

(2E)-3-(4-Chlorophenyl)-N-[(1S)-2-oxo-2-[[2-oxo-2-[4-(3,3,3-trifluoropropyl)-1-piperazinyl]ethyl]amino]-1-(2-pyridylmethyl)ethyl]-2-propenamide To a mixture of [[(2S)-2-[[(2E)-3-(4-chlorophenyl)-2propenoyl]amino]-3-(2-pyridyl)propanoyl]amino]acetic acid (38.8 g), 1-(3,3,3-trifluoropropyl)piperazine dihydrochloride (25.5 g), 1-hydroxybenzotriazole (14.9 g) and 1-(3-dimethylaminopropyl)-3-ethylcarbodiimide hydrochloride (21.1 g) in N,N-dimethylformamide (250 ml) was added dropwise N,N-diisopropylethylamine (38.3 ml) at 10° C. over 50 minutes. The mixture was warmed to room temperature and stirred for 2 hours. The reaction mixture was poured into ice-cold saturated aqueous sodium hydrogencarbonate solution (750 ml). The mixture was extracted three times with ethyl acetate (total 2500 ml) and washed successively with water (500 ml×3) and brine (200 ml). The organic layer was dried over anhydrous magnesium sulfate and concentrated. The residue was purified by silica gel column chromatography (eluent; 12% methanol in ethyl acetate) to give the title compound (37.0 g) as a white amorphous solid, which was recrystallized from ethyl acetate.

ESI-MS: 552.1(M+H)

¹H-NMR (300 MHz, CDCl₃) δ 8.55 (dd, J=5 Hz,2 Hz, 1H), 8.00 (t, J=4 Hz, 1H), 7.91 (d, J=7 Hz, 1H), 7.63 (td, J=8,2 Hz, 1H), 7.60 (d, J=16 Hz, 1H), 7.45 (d, J=9 Hz, 2H), 7.35 (d, J=9 Hz, 2H), 7.25 (d, J=8 Hz, 1H), 7.18 (dd, J=8 Hz,5 Hz, 1H), 6.49 (d, J=16 Hz, 1H), 5.05–4.97 (m, 1H), 4.01 (d, J=4 Hz, 2H), 3.68–3.52 (m, 2H), 3.46–3.34 (m, 3H), 3.25 (dd, J=15 Hz,5 Hz, 1H), 2.64–2.57 (m, 2H), 2.43 (q, J=5 Hz, 4H), 2.37–2.21 (m, 2H).

Preparation 21

(±)-tert-Butyl 3-methylpiperazine-1-carboxylate

To a solution of 2-methylpiperazine (2.2 g) in tetrahydrofuran (15 ml) was added di-tert-butyl dicarbonate (4.0 g) slowly under ice-cooling, and the mixture was stirred at room temperature for 3.5 hours. Then the reaction mixture was diluted with ethyl acetate (20 ml), washed successively with water and brine, and dried over magnesium sulfate. The solvent was evaporated to give the title compound as a colorless oil. The obtained compound was used for the next step without further purification.

¹H-NMR (300 MHz, CDCl₃) δ 1.04 (d, J=5 Hz, 3H), 1.45 (s, 9H), 2.40 (br, 1H), 2.65–2.86 (m, 4H), 2.88–3.08 (m, 1H), 3.75–4.15(m, 2H).

Preparation 22

(±)-tert-Butyl 3-methyl-4-(4-nitrophenyl)piperazine-1-carboxylate

A mixture of (±)-tert-butyl 3-methylpiperazine-1-carboxylate (1.5 g), 1-fluoro-4-nitrobenzene (1.06 g) and potassium carbonate (2.07 g) in dimethyl sulfoxide (15 ml) was stirred at 120° C. for 15 hours. The reaction mixture was cooled to room temperature and poured into water (30 ml). The mixture was extracted with ethyl acetate three times. The combined organic layers were washed successively with water (twice) and brine, and dried over magnesium sulfate. The solvent was removed under reduced pressure. The residue was purified by silica gel column chromatography (hexane-ethyl acetate 2:1) to give the title compound as a white solid.

¹H-NMR (300 MHz, CDCl₃) δ 1.18 (d, J=5 Hz, 3H), 1.48 (s, 9H), 2.99–3.31 (m, 3H), 3.55 (td, J=2 Hz,9 Hz, 1H), 3.85–4.26 (m, 3H), 6.76 (d, J=8 Hz, 2H), 8.12 (d, J=8 Hz, 2H).

Preparation 23

(±)-tert-Butyl 3-methyl-4-(4-aminophenyl)piperazine-1-carboxylate

To a mixture of (±)-tert-butyl 3-methyl-4-(4-nitrophenyl)piperazine-1-carboxylate (870 mg) and iron powder (378 mg) in ethanol (16 ml) was added an aqueous solution (4 ml) of ammonium chloride (116 mg) at room temperature. The resulting suspension was refluxed for 2 hours with vigorous stirring. The reaction mixture was cooled to room temperature, and the resulting solid was filtered through celite and thoroughly washed with ethyl acetate. The filtrate was separated, and the aqueous layer was extracted with ethyl acetate twice. The organic layers were combined and washed successively with saturated aqueous sodium hydrogencarbonate solution and brine. The solvent was evaporated to give the title compound as a yellow oil.

¹H-NMR (300 MHz, CDCl₃) δ 0.87 (d, J=6 Hz, 3H), 1.47 (8, 9H), 2.78–3.04 (m, 2H), 3.10–3.35 (m, 2H), 3.36–3.81 (m, 3H), 6.63 (d, J=8 Hz, 2H), 6.84 (d, J=8 Hz, 2H).

Preparation 24

(±)-tert-Butyl 3-methyl-4-phenylpiperazine-1-carboxylate

To a solution of (±)-tert-butyl 3-methyl-4-(4-aminophenyl)piperazine-1-carboxylate (325 mg) in 50% hypophosphorous acid (1.27 ml) containing copper(I) oxide (8.0 mg) was added dropwise a solution of sodium nitrite (92 mg) in water (2 ml) at 0° C. with stirring. After 2 hours, the reaction mixture was made alkaline with 40% NaOH solution and extracted with ethyl acetate twice. The organic layers were combined and washed with water and brine. The solvent was evaporated, and the residue was purified by silica gel column chromatography (hexane-ethyl acetate 1:1) to give the title compound in a pure form as colorless oil.

$^1$H-NMR (300 MHz, CDCl$_3$) δ 0.99 (d, J=5 Hz, 3H), 1.46 (s, 9H), 3.04–3.34 (m, 3H), 3.38 (dd, J=14 Hz,2 Hz, 11), 3.70–4.18 (m, 3H), 6.84–6.93 (m, 3H), 7.25 (dd, J=8 Hz,9 Hz, 2H).

Preparation 25

(±)-1-Phenyl-2-methylpiperazine hydrochloride (±)-tert-Butyl 3-methyl-4-phenylpiperazine-1-carboxylate (142 mg) was dissolved in 4N hydrogen chloride in ethyl acetate (5 ml). After stirring for 15 minutes, the solvent was removed under reduced pressure to give the title compound as a slightly yellow solid.

$^1$H-NMR (300 MHz, CDCl$_3$) δ 1.07 (d, 3H, J=5 Hz), 3.32 (br, 3H), 3.47 (br, 3H), 3.77 (br, 1H), 4.27 (br, 1H), 7.20(br, 1H), 7.46 (br, 4H).

EXAMPLE 20

5-Chloro-N-[(1S)-2-[[2-(3-methyl-4-phenyl-1-piperazinyl)-2-oxoethyl]amino]-2-oxo-1-(2-pyridylmethyl)ethyl]-1-benzofuran-2-carboxamide The title compound was obtained from (±)-1-phenyl-2-methylpiperazine hydrochloride and [[(2S)-2-[[(5-chloro-1-benzofuran-2-yl)carbonyl]amino]-3-(2-pyridyl)propanoyl]amino]-acetic acid in substantially the same manner as in Example 3.

$^1$H-NMR (300 MHz, CDCl$_3$) δ 1.62 (s, 3H), 3.04–4.30 (m, 10H), 5.11 (td, J=6 Hz,6 Hz, 1H), 6.89 (d, J=9 Hz, 2H), 6.91 (br, 1H), 7.18–7.31 (m, 4H), 7.37–7.51 (m, 4H), 7.63 (dd, J=2 Hz,9 Hz, 2H), 8.08–8.25 (m, 2H), 8.62 (d, J=4 Hz, 1H), 8.70–8.83 (m, 1H).

EXAMPLE 21

(2E)-3-(4-Chlorophenyl)-N-[(1S)-2-oxo-2-[[2-oxo-2-[4-(4-trifluoromethylphenyl)-1-piperazinyl]ethyl]amino]-1-(2-pyridylmethyl)ethyl]-2-propenamide The title compound was obtained from 1-(4-trifluoromethyl-phenyl)piperazine and [[(2S)-2-[[(2E)-3-(4-chlorophenyl)-2-propenoyl]amino]-3-(2-pyridyl)propanoyl]amino]acetic acid in substantially the same manner as in Example 3.

$^1$H-NMR (300 MHz, CDCl$_3$) δ 3.16–3.35 (m, 6H), 3.58 (t, J=3 Hz, 2H), 3.75 (t, J=3 Hz, 2H), 4.09 (s, 2H), 5.01 (t, J=6 Hz, 1H), 6.49 (d, J=14 Hz, 1H), 6.91 (d, J=8 Hz, 2H), 7.28 (dd, J=6 Hz,7 Hz, 1H), 7.22–7.38 (m, 5H), 7.40–7.55 (m, 4H), 7.63 (td, J=6 Hz,1 Hz, 1H), 7.86–8.00 (m, 1H), 8.52 (d, J=4 Hz, 1H).

Preparation 26 tert-Butyl (1S)-2-[4-(4-chlorophenyl)-1-piperazinyl]-1-methyl-2-oxoethylcarbamate The title compound was obtained from 1-(4-chlorophenyl)-piperazine hydrochloride and N-(tert-butoxycarbonyl)-L-alanine in substantially the same manner as in Preparation 3.

$^1$H-NMR (300 MHz, CDCl$_3$) δ 1.33 (d, J=7 Hz, 3H), 1.44 (s, 9H), 3.10–3.19 (m, 4H), 3.57–3.89 (m, 4H), 4.67 (quintet, J=7 Hz, 1H), 5.51 (d, J=7 Hz, 1H), 6.85 (d, J=8 Hz, 2H), 7.23 (d, J=8 Hz, 2H).

MS(m/z): 368(M$^+$+1), 312(bp)

Preparation 27

(2S)-1-[4-(4-Chlorophenyl)-1-piperazinyl]-1-oxo-2-propanamine dihydrochloride

The title compound was obtained from tert-butyl (1S)-2-[4-(4-chlorophenyl)-1-piperazinyl]-1-methyl-2-oxoethylcarbamate in substantially the same manner as in Preparation 2.

$^1$H-NMR (300 MHz, DMSO-d$_6$) δ 1.34 (d, J=7 Hz, 3H), 3.05–3.80 (m, 4H), 3.53–3.80 (m, 4H), 4.43 (t, J=7 Hz, 1H), 7.06 (d, J=8 Hz, 2H), 7.30 (d, J=8 Hz, 2H), 8.30 (s, 2H).

MS(m/z): 268(M$^+$,bp)

Preparation 28 tert-Butyl (1S)-2-[[(1S)-2-[4-(4-chlorophenyl)-1-piperazinyl]-1-methyl-2-oxoethyl]amino]-2-oxo-1-(2-pyridyl-methyl)ethylcarbamate The title compound was obtained from (2S)-1-[4-(4-chlorophenyl)-1-piperazinyl]-1-oxo-2-propanamine dihydrochloride and (2S)-2-(tert-butoxycarbonylamino)-3-(2-pyridyl)propanoic acid in substantially the same manner as in Preparation 3.

$^1$H-NMR (300 MHz, CDCl$_3$) δ 1.03 (d, J=7 Hz, 1H), 1.11 (d, J=7 Hz, 3H), 1.43 (s, 9H), 3.05–3.18 (m, 4H), 3.32–3.40 (m, 1H), 3.55–3.83 (m, 4H), 4.54–4.60 (m, 1H), 4.82 (d, J=7 Hz, 1H), 6.45 (d, J=7 Hz, 1H), 6.83 (d, J=8 Hz, 2H), 7.13–7.24 (m, 4H), 7.52 (d, J=7 Hz, 1H), 7.59 (ddd, J=7 Hz,7 Hz,2 Hz, 1H), 8.52 (d, J=2 Hz, 1H).

MS(m/z): 516(M$^+$,bp)

Preparation 29

(2S)-2-Amino-N-[(1S)-2-[4-(4-chlorophenyl)-1-piperazinyl]-1-methyl-2-oxoethyl]-3-(2-pyridyl)propanamide trihydrochloride The title compound was obtained from tert-butyl (1S)-2-[[(1S)-2-[4-(4-chlorophenyl)-1-piperazinyl]-1-methyl-2-oxoethyl]amino]-2-oxo-1-(2-pyridylmethyl)ethylcarbamate in substantially the same manner as in Preparation 4.

$^1$H-NMR (300 MHz, DMSO-d$_6$) δ 1.24 (d, J=7 Hz, 3H), 1.26 (t, J=7 Hz, 1H), 3.14 (t, J=5 Hz, 4H), 3.33–3.55 (m, 2H), 3.60 (t, J=5 Hz, 4H), 4.71 (quintet, J=7 Hz, 1H), 7.00 (d, J=8 Hz, 2H), 7.28 (d, J=8 Hz, 2H), 7.64–7.74 (m, 2H), 8.19 (t, J=7 Hz, 1H), 8.47 (s, 2H), 8.73 (d, J=8 Hz, 1H), 8.91 (d, J=8 Hz, 1H).

MS(m/z):416(M$^+$+1), 85(bp)

EXAMPLE 22

5-Chloro-N-[(1S)-2-[[(1S)-2-[4-(4-chlorophenyl)-1-piperazinyl]-1-methyl-2-oxoethyl]amino]-2-oxo-1-(2-pyridyl-methyl)ethyl]-1-benzofuran-2-carboxamide The title compound was obtained from (2S)-2-amino-N-[(1S)-2-[4-(4-chlorophenyl)-1-piperazinyl]-1-methyl-2-oxoethyl]-3-(2-pyridyl)propanamide trihydrochloride and 5-chloro-1-benzofuran-2-carboxylic acid in substantially the same manner as in Example 1.

$^1$H-NMR (300 MHz, CDCl$_3$) δ 1.19 (d, J=7 Hz, 3H), 3.05–3.16 (m, 4H), 3.40 (ABXY, J=15 Hz,15 Hz,7.5 Hz,7 Hz, 2H), 3.56–3.80 (m, 4H), 4.84 (quintet, J=7 Hz, 1H), 5.05 (q, J=7 Hz, 1H), 6.83 (d, J=8 Hz, 2H), 7.19–7.28 (m, 4H), 7.37 (d, J=2 Hz, 1H), 7.45 (AB, J=8,8 Hz, 2H), 7.60–7.67 (m, 2H), 8.03 (d, J=7.5 Hz, 1H), 8.61 (d, J=7 Hz, 1H), 8.80 (d, J=8 Hz, 1H).

m.p. 152–155° C.

MS(m/z): 594(M$^+$), 115(bp)

EXAMPLE 23

(2E)-3-(4-Chlorophenyl)-N-[(1S)-2-[[(1S)-2-[4-(4-chlorophenyl)-1-piperazinyl]-1-methyl-2-oxoethyl]amino]-2-oxo-1-(2-pyridylmethyl)ethyl]-2-propenamide The title compound was obtained from (2S)-2-amino-N-[(1S)-2-[4-(4-chlorophenyl)-1-piperazinyl]-1-methyl-2-oxoethyl]-3-(2-pyridyl)propanamide trihydrochloride and 4-chlorocinnamic acid in substantially the same manner as in Example 2.

$^1$H-NMR (300 MHz, CDCl$_3$) δ 1.14 (d, J=7 Hz, 3H), 3.05–3.15 (m, 4H), 3.33 (ABXY, J=15 Hz, 15 Hz,7.5 Hz,7

Hz, 2H), 3.54–3.83 (m, 4H), 4.80 (quintet, J=7 Hz, 1H), 4.95 (q, J=7 Hz, 1H), 6.49 (d, J=15 Hz, 1H), 6.83 (d, J=8 Hz, 2H), 7.17–7.28 (m, 4H), 7.40 (AB, J=8 Hz,7.5 Hz, 4H), 7.57–7.65 (m, 2H), 7.82 (d, J=7.5 Hz, 1H), 7.93 (d, J=7.5 Hz, 1H), 8.55 (d, J=7 Hz, 1H).

m.p. 179–181° C.

MS(m/z): 580(M$^+$), 115(bp)

Preparation 30 tert-Butyl (1S)-1-methyl-2-oxo-2-(4-phenyl-1-piperazinyl)ethylcarbamate

The title compound was obtained from 1-phenylpiperazine and N-(tert-butoxycarbonyl)-L-alanine in substantially the same manner as in Preparation 3.

$^1$H-NMR (300 MHz, CDCl$_3$) δ 1.33 (d, J=7 Hz, 3H), 1.44 (s, 9H), 3.16–3.22 (m, 4H), 3.59–3.89 (m, 4H), 4.67 (quintet, J=7 Hz, 1H), 5.54 (d, J=7 Hz, 1H), 6.86–6.95 (m, 3H), 7.29–7.37 (m, 21).

MS(m/z): 334(M$^+$+1), 115(bp)

Preparation 31

(2S)-1-Oxo-1-(4-phenyl-1-piperazinyl)-2-propanamine dihydrochloride

The title compound was obtained from tert-butyl (1S)-1-methyl-2-oxo-2-(4-phenyl-1-piperazinyl)ethylcarbamate in substantially the same manner as in Preparation 2.

$^1$H-NMR (300 MHz, DMSO-d$_6$) δ 1.34(d, J=7 Hz, 3H), 3.05–3.15(m, 1H), 3.20–3.30(m, 4H), 3.55–3.85(m, 4H), 6.83–7.07(m, 3H), 7.18–0.44(m, 2H), 8.23(s, 2H).

MS(m/z): 234(M$^+$+1), 169(bp)

Preparation 32 tert-Butyl (1S)-2-[[(1S)-1-methyl-2-oxo-2-(4-phenyl-1-piperazinyl)ethyl]amino]-2-oxo-1-(2-pyridylmethyl)ethylcarbamate The title compound was obtained from (2S)-1-oxo-1-(4-phenyl-1-piperazinyl)-2-propanamine dihydrochloride and (2S)-2-(tert-butoxycarbonylamino)-3-(2-pyridyl)propanoic acid in substantially the same manner as in Preparation 3.

$^1$H-NMR (300 MHz, CDCl$_3$) δ 1.22 (d, J=7 Hz, 3H), 1.43 (s, 9H), 3.08–3.20 (m, 4H), 3.31–3.42 (m, 1H), 3.55–3.80 (m, 4H), 4.57 (d, J=7 Hz, 1H), 4.83 (quintet, J=7 Hz, 1H), 6.45 (d, J=7 Hz, 1H), 6.87–6.93 (m, 4H), 7.12–7.20 (m, 3H), 7.30 (d, J=8 Hz, 1H), 7.54–7.62 (m, 2H), 8.51 (d, J=7 Hz, 1H).

MS(m/z): 482(M$^+$+1), 74(bp)

Preparation 33

(2S)-2-Amino-N-[(1S)-1-methyl-2-oxo-2-(4-phenyl-1-piperazinyl)ethyl]-3-(2-pyridyl)propanamide trihydrochloride The title compound was obtained from tert-butyl (1S)-2-[[(1S)-1-methyl-2-oxo-2-(4-phenyl-1-piperazinyl)ethyl]amino]-2-oxo-1-(2-pyridylmethyl)ethylcarbamate in substantially the same manner as in Preparation 4.

$^1$H-NMR (300 MHz, DMSO-d$_6$) δ 1.25 (d, J=7 Hz, 3H), 3.15–3.25 (m, 4H), 3.35–3.55 (m, 3H), 3.69 (broad s, 4H), 4.83 (quintet, J=7 Hz, 1H), 6.93 (t, J=8 Hz, 1H), 7.09 (d, J=8 Hz, 2H), 7.25 (d, J=8 Hz, 2H), 7.67–7.77 (m, 2H), 8.23 (t, J=8 Hz, 1H), 8.49 (s, 2H), 8.74 (d, J=8 Hz, 1H), 8.93 (d, J=8 Hz, 1H).

MS(m/z): 382(M$^{30}$ +1), 169(bp)

EXAMPLE 24

(2E)-3-(4-Chlorophenyl)-N-[(1S)-2-[[(1S)-1-methyl-2-oxo-2-(4-phenyl-1-piperazinyl)ethyl]amino]-2-oxo-1-(2-pyridylmethyl)ethyl]-2-propenamide The title compound was obtained from (2S)-2-amino-N-[(1S)-1-methyl-2-oxo-2-(4-phenyl-1-piperazinyl)ethyl]-3-(2-pyridyl)-propanamide trihydrochloride and 4-chlorocinnamic acid in substantially the same manner as in Example 2.

$^1$H-NMR (300 MHz, CDCl$_3$) δ 1.14 (d, J=7 Hz, 3H), 3.07–3.18 (m, 4H), 3.35 (ABXY, J=15 Hz,15 Hz,7.5 Hz,7 Hz, 2H), 3.53–3.83 (m, 4H), 4.79 (quintet, J=7 Hz, 1H), 4.96 (q, J=7 Hz, 1H), 6.49 (d, J=15 Hz, 1H), 6.89–7.04 (m, 3H), 7.17–7.32 (m, 4H), 7.40 (AB, J=8 Hz,7.5 Hz, 4H), 7.58–7.67 (m, 2H), 7.85 (d, J=7.5 Hz, 1H), 7.92 (d, J=7.5 Hz, 1H), 8.55 (d, J=7 Hz, 1H).

m.p. 178–179° C.

MS(m/z): 475(M$^+$), 79(bp)

EXAMPLE 25

5-Chloro-N-[(1S)-2-[[2-[(2S)-2-(methoxymethyl)-4-phenyl-1-piperazinyl]-2-oxoethyl]amino]-2-oxo-1-(2-pyridylmethyl)ethyl]-1-benzofuran-2-carboxamide The title compound was obtained from [[(2S)-2-[[(5-chloro-1-benzofuran-2-yl)carbonyl]amino]-3-(2-pyridyl)propanoyl]-amino]acetic acid and (S)-2-methoxymethyl-4-phenylpiperazine in substantially the same manner as in Example 3.

m.p. 95–100° C.

MS: (ES+)590.14

$^1$H-NMR (300 MHz, DMSO-d$_6$) δ 2.47–3.05 (m, 5H), 3.17–3.31 (m, 4H), 3.50–3.75 (m, 4H), 3.87–4.31 (m, 3H), 4.95–5.05 (br B, 1H), 6.76–6.94 (m, 3H), 7.15–7.87 (m, 9H), 8.13–8.24 (m, 1H), 8.47–8.50 (m, 1H), 9.04 (d, J=9 Hz, 1H).

EXAMPLE 26

5-Chloro-N-[(1S)-2-[[2-[(2S)-2-(hydroxymethyl)-4-phenyl-1-piperazinyl]-2-oxoethyl]amino]-2-oxo-1-(2-pyridylmethyl)ethyl]-1-benzofuran-2-carboxamide The title compound was obtained from [[(2S)-2-[[(5-chloro-1-benzofuran-2-yl)carbonyl]amino]-3-(2-pyridyl) propanoyl]-amino]acetic acid and (s)-2-hydroxymethyl-4-phenylpiperazine in substantially the same manner as in Example 3.

m.p. 115–120° C.

MS: (ES+)576.12

$^1$H-NMR (300 MHz, DMSO-d$_6$) δ 2.50–3.03 (m, 4H), 3.26–3.48 (m, 3H), 3.51–4.32 (m, 6H), 4.96–5.06 (m, 2H), 6.76–6.95 (m, 3H), 7.16–7.87 (m, 9H), 8.10–8.23 (m, 1H), 8.50 (d, J=6 Hz, 1H), 9.06 (d, J=9 Hz, 1H).

EXAMPLE 27

5-Chloro-N-[(1S)-2-[[2-[4-(4-methoxyphenyl)-1-piperazinyl]-2-oxoethyl]amino]-2-oxo-1-(2-pyridylmethyl) ethyl]-1-benzofuran-2-carboxamide The title compound was obtained from [[(2S)-2-[[(5-chloro-1-benzofuran-2-yl)carbonyl]amino]-3-(2-pyridyl) propanoyl]-amino]acetic acid and 1-(4-methoxyphenyl) piperazine dihydrochloride in substantially the same manner as in Example 3.

$^1$H-NMR (300 MHz, CDCl$_3$) δ 2.96–3.07 (m, 4H), 3.34 (dd, J=15, 7 Hz, 1H), 3.44–3.57 (m, 3H), 3.70–3.80 (m, 2H), 3.77 (s, 3H), 4.09 (d, J=5 Hz, 2H), 5.11 (m, 1H), 6.79–6.92 (m, 4H), 7.20 (m, 1H), 7.27 (d, J=9 Hz, 1H), 7.35–7.42 (m, 2H), 7.49 (d, J=9 Hz, 1H), 7.60–7.69 (m, 2H), 8.20 (m, 1H), 8.63 (d, J=5 Hz, 1H), 8.76 (d, J=7 Hz, 1H).

33

EXAMPLE 28

(2E)-3-(4-Chlorophenyl)-N-[(1S)-2-[[2-[4-(2-methylphenyl)-1-piperazinyl]-2-oxoethyl]amino]-2-oxo-1-(2-pyridylmethyl)ethyl]-2-propenamide The title compound was obtained from [[(2S)-2-[[(2E)-3-(4-chlorophenyl)-2-propenoyl]amino]-3-(2-pyridyl)propanoyl]amino]-acetic acid and 1-(2-methylphenyl)piperazine hydrochloride in substantially the same manner as in Example 3.

$^1$H-NMR (300 MHz, CDCl$_3$) δ 2.31 (s, 3H), 2.77–2.93 (m, 4H), 3.28 (dd, J=15 Hz,7 Hz, 10), 3.37–3.56 (m, 3H), 3.68–3.80 (m, 2H), 4.07 (d, J=5 Hz, 2H), 5.04 (m, 1H), 6.50 (d, J=15 Hz, 1H), 6.89–7.08 (m, 2H), 7.09–7.50 (m, 8H), 7.53–7.69 (m, 2H), 7.95 (d, J=7 Hz, 1H), 8.06 (m, 1H), 8.56 (d, J=5 Hz, 1H).

EXAMPLE 29

5-Chloro-N-[(1S)-2-[[2-[4-(4-chlorophenyl)-1-piperazinyl]-2-oxoethyl]amino]-1-[(5-methoxy-2-pyridyl)methyl]-2-oxoethyl]-1-benzofuran-2-carboxamide The title compound was obtained in substantially the same manner as in Preparation 3, Preparation 4 and Example 1 using (2S)-2-(tert-butoxycarbonylamino)-3-(5-methoxy-2-pyridyl)-propanoic acid instead of (2S)-2-(tert-butoxycarbonylamino)-3-(2-pyridyl)propanoic acid.

$^1$H-NMR (300 MHz, CDCl$_3$) δ 3.04–3.16 (m, 4H), 3.22–3.34 (m, 1H), 3.49–3.64 (m, 3H), 3.70–3.80 (m, 2H), 3.86 (s, 3H), 4.08–4.15 (m, 2H), 5.18–5.27 (m, 1H), 6.82 (d, J=8 Hz, 2H), 7.09–7.40 (m, 6H), 7.45 (d, J=8 Hz, 1H), 7.61–7.64 (m, 1H), 8.10–8.20 (m, 2H), 8.38 (d, J=8 Hz, 1H).

MS(ESI): m/z 610 (M+1).

EXAMPLE 30

5-Chloro-N-[(1S)-2-[[2-[4-(4-chlorophenyl)-1-piperazinyl]-2-oxoethyl]amino]-2-oxo-1-(3-pyridylmethyl)ethyl]-1-benzofuran-2-carboxamide The title compound was obtained in substantially the same manner as in Preparation 3, Preparation 4 and Example 1 using (2S)-2-(tert-butoxycarbonylamino)-3-(3-pyridyl)propanoic acid instead of (2S)-2-(tert-butoxycarbonylamino)-3-(2-pyridyl)-propanoic acid.

$^1$H-NMR (300 MHz, CDCl$_3$) δ 3.05–3.35 (m, 6H), 3.49–3.60 (m, 2H), 3.70–3.80 (m, 2H), 3.98–4.20 (m, 2H), 4.95–5.06 (m, 1H), 6.83 (d, J=8 Hz, 2H), 7.05 (br s, 1H), 7.17–7.46 (m, 7H), 7.55–7.65 (m, 2H), 8.42–8.52 (m, 2H).

MS(ESI): m/z 580 (M+1).

EXAMPLE 31

5-Chloro-N-[(1S)-2-[[2-[4-(4-chlorophenyl)-1-piperazinyl]-2-oxoethyl]amino]-2-oxo-1-(4-pyridylmethyl)ethyl]-1-benzofuran-2-carboxamide The title compound was obtained in substantially the same manner as in Preparation 3, Preparation 4 and Example 1 using (2S)-2-(tert-butoxycarbonylamino)-3-(4-pyridyl)propanoic acid instead of (2S)-2-(tert-butoxycarbonylamino)-3-(2-pyridyl)-propanoic acid.

$^1$H-NMR (300 MHz, CDCl$_3$) δ 3.07–3.34 (m, 6H), 3.50–3.58 (m, 2H), 3.72–3.80 (m, 2H), 3.96–4.17 (m, 2H), 4.98–5.08 (m, 1H), 6.83 (d, J=8 Hz, 2H), 6.96–7.03 (m, 1H), 7.15–7.27 (m, 5H), 7.35–7.46 (m, 3H), 7.62–7.65 (m, 1H), 8.52 (br s, 2H).

MS(ESI): m/z 580 (M+1).

This application is based on application No. PQ3868 filed in Australia on Nov. 4, 1999, the content of which is incorporated hereinto by reference.

34

What is claimed is:
1. A compound of the formula (I):

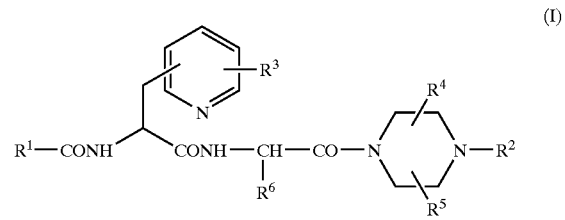

wherein
$R^1$ is benzofuranyl substituted by halogen, or styryl substituted by halogen,
$R^2$ is phenyl, pyridyl, thienyl or thiazolyl, each of which is optionally substituted by one or more substituents selected from the group consisting of lower alkyl, lower alkoxy, halogen and trihalo(lower)alkyl, or lower alkyl optionally substituted by one or more halogen atoms,
$R^3$ is hydrogen or lower alkoxy,
$R^4$ and $R^5$ are the same or different and each is hydrogen, lower alkyl, hydroxy($C_1$–$C_6$)alkyl, hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl, 6-hydroxyhexyl, lower alkoxy(lower)alkyl, ($C_1$–$C_6$)alkoxy($C_1$–$C_6$)alkyl, methoxymethyl, 1-methoxyethyl, 2-methoxyethyl, 1-methoxypropyl, 2-methoxypropyl, 3-methoxypropyl, ethoxymethyl, 2-ethoxyethyl, 3-ethoxypropyl or propoxymethyl, and
$R^6$ is hydrogen or lower alkyl,
or a pharmaceutically acceptable salt thereof.

2. The compound of claim 1, wherein $R^1$ is benzofuranyl substituted by halogen, or a pharmaceutically acceptable salt thereof.

3. The compound of claim 1, wherein $R^1$ is styryl substituted by halogen, or a pharmaceutically acceptable salt thereof.

4. The compound of claim 1, wherein $R^2$ is phenyl, pyridyl, thienyl or thiazolyl, each of which is optionally substituted by one or more substituents selected from the group consisting of lower alkyl, lower alkoxy, halogen and trihalo(lower)alkyl, or trihalo(lower)alkyl, or a pharmaceutically acceptable salt thereof.

5. The compound of claim 4, wherein $R^2$ is phenyl optionally substituted by one or more substituents selected from the group consisting of lower alkyl, lower alkoxy, halogen and trihalo(lower)alkyl, or trihalo(lower)alkyl, or a pharmaceutically acceptable salt thereof.

6. The compound of claim 4, wherein $R^2$ is pyridyl, thienyl or thiazolyl, each of which is optionally substituted by one or more substituents selected from the group consisting of halogen and trihalo(lower)alkyl, or a pharmaceutically acceptable salt thereof.

7. The compound of claim 1, wherein $R^3$ is hydrogen, or a pharmaceutically acceptable salt thereof.

8. The compound of claim 1, wherein $R^3$ is lower alkoxy, or a pharmaceutically acceptable salt thereof.

9. The compound of claim 1, wherein $R^4$ and $R^5$ are hydrogen, or a pharmaceutically acceptable salt thereof.

10. The compound of claim 1, wherein $R^4$ and $R^5$ are lower alkyl, or a pharmaceutically acceptable salt thereof.

11. The compound of claim 1, wherein $R^4$ and $R^5$ are hydroxy($C_1$–$C_6$)alkyl, hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl, 6-hydroxyhexyl, lower alkoxy(lower)alkyl, $(C_1-C_6)$alkoxy$(C_1-C_6)$alkyl, methoxymethyl, 1-methoxyethyl, 2-methoxyethyl, 1-methoxypropyl, 2-methoxypropyl, 3-methoxypropyl, ethoxymethyl, 2-ethoxyethyl, 3-ethoxypropyl or propoxymethyl, or a pharmaceutically acceptable salt thereof.

12. The compound of claim 1, wherein $R^6$ is hydrogen.

13. The compound of claim 1, wherein $R^6$ is lower alkyl.

14. A pharmaceutical composition comprising the compound of claim 1 or a pharmaceutically acceptable salt thereof in admixture with a pharmaceutically acceptable carrier.

15. The pharmaceutical composition of claim 14, which further comprises FK506.

16. A method of making the pharmaceutical composition of claim 14, comprising combining the compound or the pharmaceutically acceptable salt thereof and the pharmaceutically acceptable carrier.

17. A method of making the pharmaceutical composition of claim 15, comprising combining the compound or the pharmaceutically acceptable salt thereof, the pharmaceutically acceptable carrier and the FK506.

18. A method of treating, arresting, alleviating, or reducing rejection of organ transplantation in a mammal, comprising administering the pharmaceutical composition of claim 15 to a mammal.

19. A method of treating, prolonging, or extending the onset of organ rejection in a human during or after organ transplantation in a human, comprising administering the pharmaceutical composition of claim 15, to a human.

* * * * *